(12) United States Patent
Ban et al.

(10) Patent No.: US 11,813,199 B2
(45) Date of Patent: *Nov. 14, 2023

(54) DISTRIBUTED ACOUSTIC DETECTOR SYSTEM

(71) Applicant: Lutronic Vision Inc., Burlington, MA (US)

(72) Inventors: Dayan Ban, Waterloo (CA); Mordehai Margalit, Zikhron Ya'akov (IL); Taeho Ha, Goyang (KR)

(73) Assignee: Lutronic Vision Inc.

( * ) Notice: Subject to any disclaimer, the term of this patent is extended or adjusted under 35 U.S.C. 154(b) by 0 days.

This patent is subject to a terminal disclaimer.

(21) Appl. No.: 18/065,466

(22) Filed: Dec. 13, 2022

(65) Prior Publication Data

US 2023/0110181 A1   Apr. 13, 2023

Related U.S. Application Data

(63) Continuation of application No. 16/759,323, filed as application No. PCT/US2017/058338 on Oct. 25, 2017, now Pat. No. 11,554,049.

(51) Int. Cl.
| | | |
|---|---|---|
| *A61F 9/009* | (2006.01) | |
| *A61F 9/008* | (2006.01) | |
| *G01N 29/07* | (2006.01) | |
| *G01N 29/24* | (2006.01) | |
| *A61F 9/00* | (2006.01) | |

(52) U.S. Cl.
CPC .............. *A61F 9/009* (2013.01); *A61F 9/008* (2013.01); *G01N 29/07* (2013.01); *G01N 29/2437* (2013.01); *A61F 2009/0035* (2013.01); *A61F 2009/00844* (2013.01); *A61F 2009/00897* (2013.01); *G01N 2291/011* (2013.01);

(Continued)

(58) Field of Classification Search
CPC .. A61F 9/009; A61F 9/008; A61F 2009/0035; A61F 2009/00844; A61F 2009/00897; G01N 29/07; G01N 29/2437; G01N 2291/011; G01N 2291/02475; G01N 2291/044; G01N 2291/106
See application file for complete search history.

(56) References Cited

U.S. PATENT DOCUMENTS

| 6,671,043 B1 | 12/2003 | Huettman |
| 2006/0111697 A1 | 5/2006 | Brinkmann et al. |

(Continued)

FOREIGN PATENT DOCUMENTS

| WO | WO95/29737 A1 | 11/1995 |
| WO | WO2012/142223 A1 | 10/2012 |
| WO | WO2015/012540 A1 | 1/2015 |

OTHER PUBLICATIONS

International Search Report and Written Opinion for International Application No. PCT/US2017/058338 dated Jan. 26, 2018, pp. 07.

*Primary Examiner* — Peter J Macchiarolo
*Assistant Examiner* — John M Royston

(57) ABSTRACT

In some examples, a distributed acoustic detector system may include a frame structure and multiple acoustic detectors. The frame structure may be configured to be retained in a laser-based ophthalmo-logical surgical system aligned to an eye of a patient during therapeutic treatment of the eye of the patient with the laser-based ophthalmological surgical system. The acoustic detectors may be coupled to the frame structure and may be spaced apart from each other and electrically separated from each other.

18 Claims, 12 Drawing Sheets

(52) U.S. Cl.
    CPC ........... *G01N 2291/02475* (2013.01); *G01N 2291/044* (2013.01); *G01N 2291/106* (2013.01)

(56)  References Cited

U.S. PATENT DOCUMENTS

| | | |
|---|---|---|
| 2009/0174884 A1 | 7/2009 | Kosterev et al. |
| 2010/0061187 A1 | 3/2010 | Sodal |
| 2013/0289450 A1 | 10/2013 | Homer |

DISTRIBUTED ACOUSTIC DETECTOR SYSTEM

CROSS-REFERENCE

This patent application is a continuation of U.S. patent application Ser. No. 16/759,323 filed Apr. 27, 2020, which is section 371 nationalization of PCT Application No. PCT/US2017/058338 filed Oct. 25, 2017, which application is incorporated herein by specific reference in its entirety.

BACKGROUND ART

Unless otherwise indicated herein, the materials described herein are not prior art to the claims in the present application and are not admitted to be prior art by inclusion in this section.

Therapeutic radiation may be administered to an eye of a patient to treat various conditions of the eye that may negatively affect vision. It may be difficult to accurately measure an exposure level of the eye to the therapeutic radiation, which can damage the eye at excess exposure levels.

SUMMARY

Techniques described herein generally relate to distributed acoustic detector systems.

In an example embodiment, a distributed acoustic detector system may include a frame structure and multiple acoustic detectors. The frame structure may be configured to be retained in a laser-based ophthalmological surgical system aligned to an eye of a patient during therapeutic treatment of the eye of the patient with the laser-based ophthalmological surgical system. The acoustic detectors may be coupled to the frame structure and may be spaced apart from each other and electrically separated from each other.

In another example embodiment, a laser-based ophthalmological surgical system may include such a distributed acoustic detector system.

In another example embodiment, a method of therapeutic radiation dosimetry may include illuminating an eye of a patient with therapeutic radiation. The therapeutic radiation may cause microbubbles to form on melanosomes of retinal pigment epithelial (RPE) cells of the eye of the patient during therapeutic treatment of the eye of the patient. The method may also include positioning such a distributed acoustic detector system to receive acoustic waves from the microbubbles formed in the eye of the patient during the therapeutic treatment of the eye of the patient with the therapeutic radiation. The method may also include detecting at the acoustic detectors acoustic waves received from the microbubbles formed in the eye of the patient. The method may also include generating detection signals by the acoustic detectors, the detection signals being indicative of an amount of therapeutic radiation exposure of the eye of the patient.

In another example embodiment, a laser-based ophthalmological surgical system may include a therapeutic radiation source, a distributed acoustic detector system, and a head fixation assembly. The head fixation assembly may be configured to position and retain a head of a patient with an eye of the patient aligned to the distributed acoustic detector system and aligned to receive therapeutic radiation emitted by the therapeutic radiation source. The distributed acoustic detector system may include a frame structure and multiple acoustic detectors. The frame structure may be configured to be retained in the laser-based ophthalmological surgical system proximate to the eye of the patient during therapeutic treatment of the eye of the patient with the laser-based ophthalmological surgical system. The acoustic detectors may be coupled to the frame structure and may be spaced apart from each other and electrically separated from each other.

In another example embodiment, a method of therapeutic radiation dosimetry may include illuminating an eye of a patient with therapeutic radiation. The therapeutic radiation may cause microbubbles to form on melanosomes of RPE cells of the eye of the patient during therapeutic treatment of the eye of the patient. The method may also include positioning a distributed acoustic detector system to receive acoustic waves from the microbubbles formed in the eye of the patient during the therapeutic treatment of the eye of the patient with the therapeutic radiation. The distributed acoustic detector system may include multiple acoustic detectors spaced apart from each other and electrically separated from each other. The method may also include detecting at the acoustic detectors acoustic waves received from the microbubbles formed in the eye of the patient. The method may also include generating detection signals by the acoustic detectors, the detection signals being indicative of an amount of therapeutic radiation exposure of the eye of the patient.

In some embodiments, a frame structure is configured to be retained in a laser-based ophthalmological surgical system and to be aligned to an eye of a patient during therapeutic treatment of the eye of the patient with the laser-based ophthalmological surgical system. In some aspects, a plurality of acoustic detectors are coupled to the frame structure at a plurality of spaced apart locations from each other and each acoustic detector being electrically separated from each other acoustic detector. In some aspects, the frame structure includes a circular perimeter and the plurality of acoustic detectors are spaced apart from each other along the circular perimeter of the frame structure. In some aspects, the frame structure includes a circular perimeter and the plurality of acoustic detectors are spaced apart from each other along the circular perimeter at substantially equal intervals.

In some embodiments, the distributed acoustic detector system can include at least one acoustic signal generator coupled to the frame structure and configured to generate and emit interrogation acoustic waves into the eye of the patient. In some aspects, the plurality of acoustic detectors is configured to detect echo acoustic waves of reflections of the interrogation acoustic waves from microbubbles formed on melanosomes of retinal pigment epithelial (RPE) cells of the eye of the patient in response to exposure to therapeutic radiation during the therapeutic treatment of the eye of the patient with the laser-based ophthalmological surgical system.

In some embodiments, the distributed acoustic detector system can include: at least one acoustic signal generator coupled to the frame structure and configured to generate and emit interrogation acoustic waves into the eye of the patient; and a processor communicatively coupled to the plurality of acoustic detectors and configured to analyze a plurality of detection signals generated by the plurality of acoustic detectors that are each representative of a detected echo acoustic wave to determine a particular location within the eye of the patient at which a microbubble formed based on a time difference of arrival of the detected acoustic wave at the plurality of acoustic detectors.

In some embodiments, the distributed acoustic detector system can include: at least one acoustic signal generator coupled to the frame structure and configured to generate and emit interrogation acoustic waves into the eye of the patient; at least one frequency detector communicatively coupled to the plurality of acoustic detectors and configured to determine frequencies of detected echo acoustic waves over time; and a processor communicatively coupled to the at least one frequency detector and configured to determine at least one time at which the microbubbles form or burst based on frequencies of the detected echo acoustic waves as a function of time.

In some embodiments, the distributed acoustic detector system can include at least one frequency detector that includes at least one of: a heterodyne frequency modulation (FM) receiver or a digital electronic circuit that includes at least one of: a field programmable gate array (FPGA); a digital signal processor (DSP); or an application specific integrated circuit (ASIC).

In some embodiments, the distributed acoustic detector system can include at least one frequency detector that includes a digital electronic circuit, wherein the digital electronic circuit is configured to determine the frequencies of detected echo acoustic waves over time by applying a Fourier transform to digitized detection signals generated by the plurality of acoustic detectors that are each representative of a detected echo acoustic wave.

In some embodiments, distributed acoustic detector system includes a plurality of acoustic signal generators configured to generate and emit interrogation acoustic waves into the eye of the patient, wherein the plurality of acoustic signal generators are controlled to generate and emit interrogation acoustic waves that constructively combine along a preferred direction toward a target location at which therapeutic radiation is targeted. In some aspects, a plurality of acoustic detectors is coupled to the frame structure at a plurality of spaced apart locations from each other and electrically separated from each other acoustic detector.

In some embodiments, the method can include: detecting acoustic waves emitted by bursting of the microbubbles; and analyzing the detection signals generated by the plurality of acoustic detectors that are each representative of a detected acoustic wave to determine a particular location within the eye of the patient at which a microbubble formed and burst based on a time difference of arrival of the detected acoustic wave at the plurality of acoustic detectors.

In some embodiments, the method can include: emitting interrogation acoustic waves from at least one acoustic signal generator into the eye of the patient; and analyzing the detection signals generated by the plurality of acoustic detectors that are each representative of a detected echo acoustic wave from the interrogation acoustic waves to determine a particular location within the eye of the patient at which a microbubble formed and burst based on a time difference of arrival of the detected echo acoustic wave at the plurality of acoustic detectors.

In some embodiments, the method can include: emitting interrogation acoustic waves from at least one acoustic signal generator into the eye of the patient, wherein detecting the acoustic waves comprises detecting echo acoustic waves of reflections of the interrogation acoustic waves from the microbubbles; determining frequencies of detected echo acoustic waves over time; and determining at least one time at which the microbubbles form or burst based on frequencies of the detected echo acoustic waves as a function of time.

In some embodiments, the method can include: digitizing each of the detection signals; and determining frequencies of detected echo acoustic waves by performing a Fourier transform of each of the digitized detection signals, wherein the echo acoustic wave are from reflections of interrogation acoustic waves from the microbubbles.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information, as well as other features of this disclosure, will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings:

DETAILED DESCRIPTION

Figure 1A:
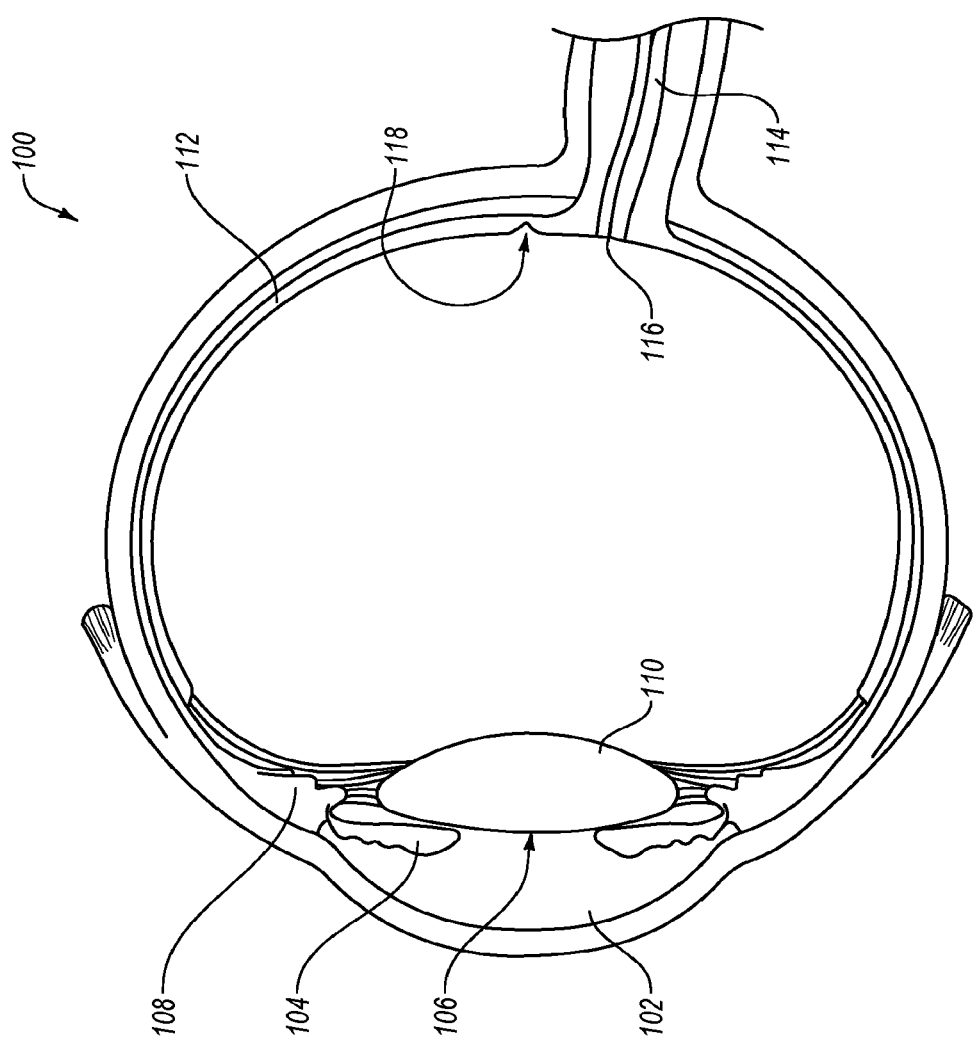
FIG. 1A is a cross-sectional view of an example human eye (hereinafter "eye")

This disclosure is generally drawn to methods, apparatus, systems, devices, and computer program products related to distributed acoustic detector systems. Such distributed acoustic detector systems may include multiple piezoelectric devices to generate and/or detect acoustic waves.

A distributed acoustic detector system in accordance with the present disclosure may include a frame structure and multiple acoustic detectors. The frame structure may be configured to be retained in a laser-based ophthalmological surgical system (hereinafter "system") aligned to an eye of a patient during therapeutic treatment of the eye of the patient with the system. The system may include a therapeutic radiation source which may emit therapeutic radiation directed to a target area of the eye of the patient. The therapeutic radiation may induce a change in the target area of the eye of the patient, such as formation and/or bursting of microbubbles, which may be measured acoustically with the distributed acoustic detector system. In particular, the acoustic detectors may generate detection signals representative of acoustic waves emitted by bursting of the microbubbles and/or of acoustic waves reflected by the microbubbles during formation and/or bursting.

In this detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. The aspects of the present disclosure, as generally described herein, and illustrated in the Figures, can be arranged, substituted, combined, separated, and designed in a wide variety of different configurations, all of which are explicitly contemplated herein.

FIG. 1A is a cross-sectional view of an example human eye (hereinafter "eye") 100, arranged in accordance with at least one embodiment described herein. The eye 100 may include a cornea 102, an iris 104, a pupil 106, a ciliary body 108, a lens 110, a retina 112, and an optic nerve 114. The retina 112 generally includes a light-sensitive layer of tissue upon which optics of the eye 100 project an image of the visual world external to the eye 100. Through a series of chemical and electrical events nerve impulses may be triggered in response to light striking the retina 112. The nerve impulses may be processed in vision centers of the brain such that the visual world may be perceived by a person.

As illustrated in FIG. 1A, the retina 112 includes an optic disc 116, sometimes referred to as the "blind spot", and a macula 118 temporal to the optic disc 116.

Figure 1B:
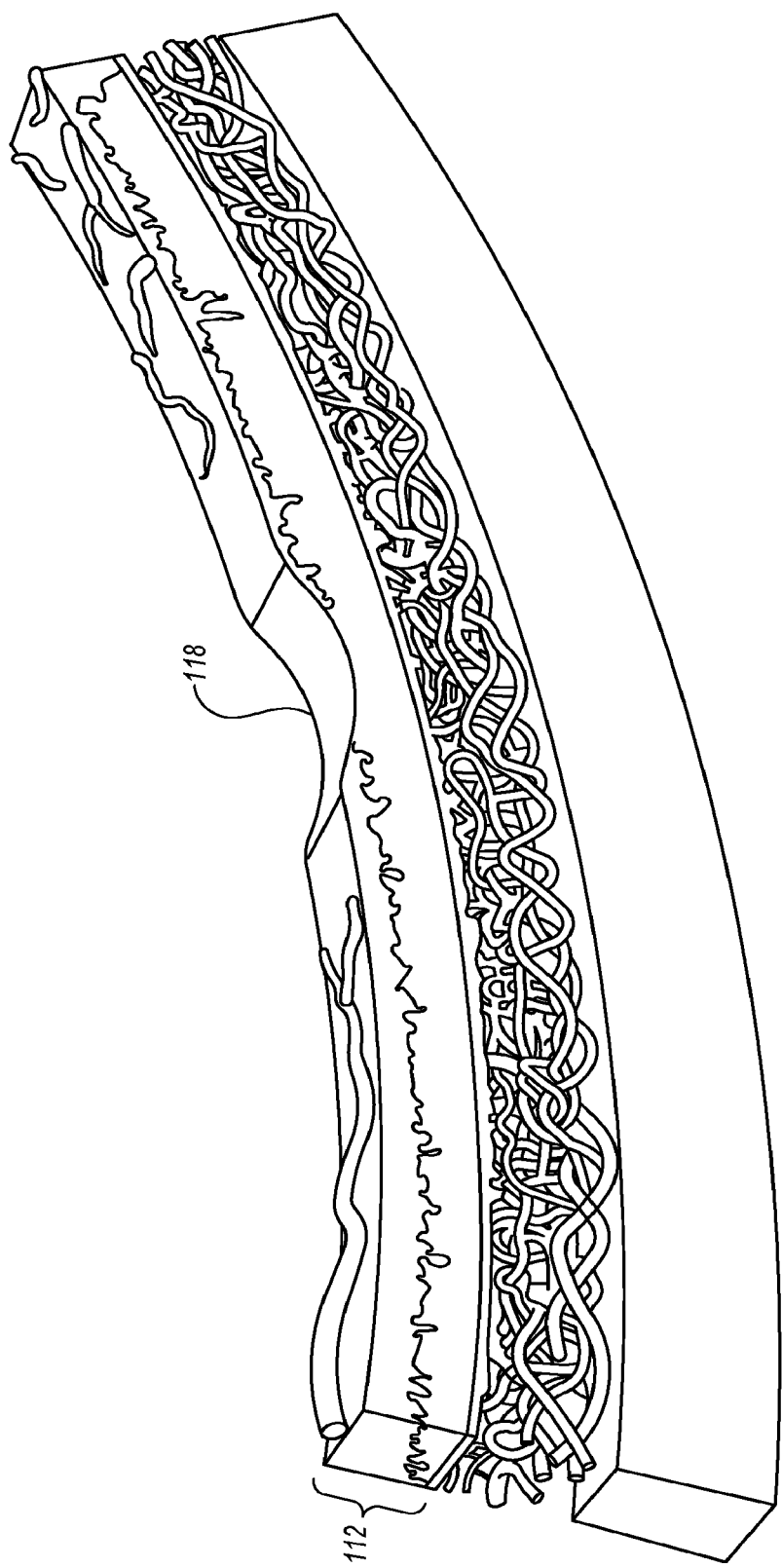
FIG. 1B is a cross-sectional perspective view of a portion of a retina and macula of FIG. 1B.

FIG. 1B is a cross-sectional perspective view of a portion of the retina 112 and the macula 118 of FIG. 1A, arranged in accordance with at least one embodiment described herein.

Figure 1C:
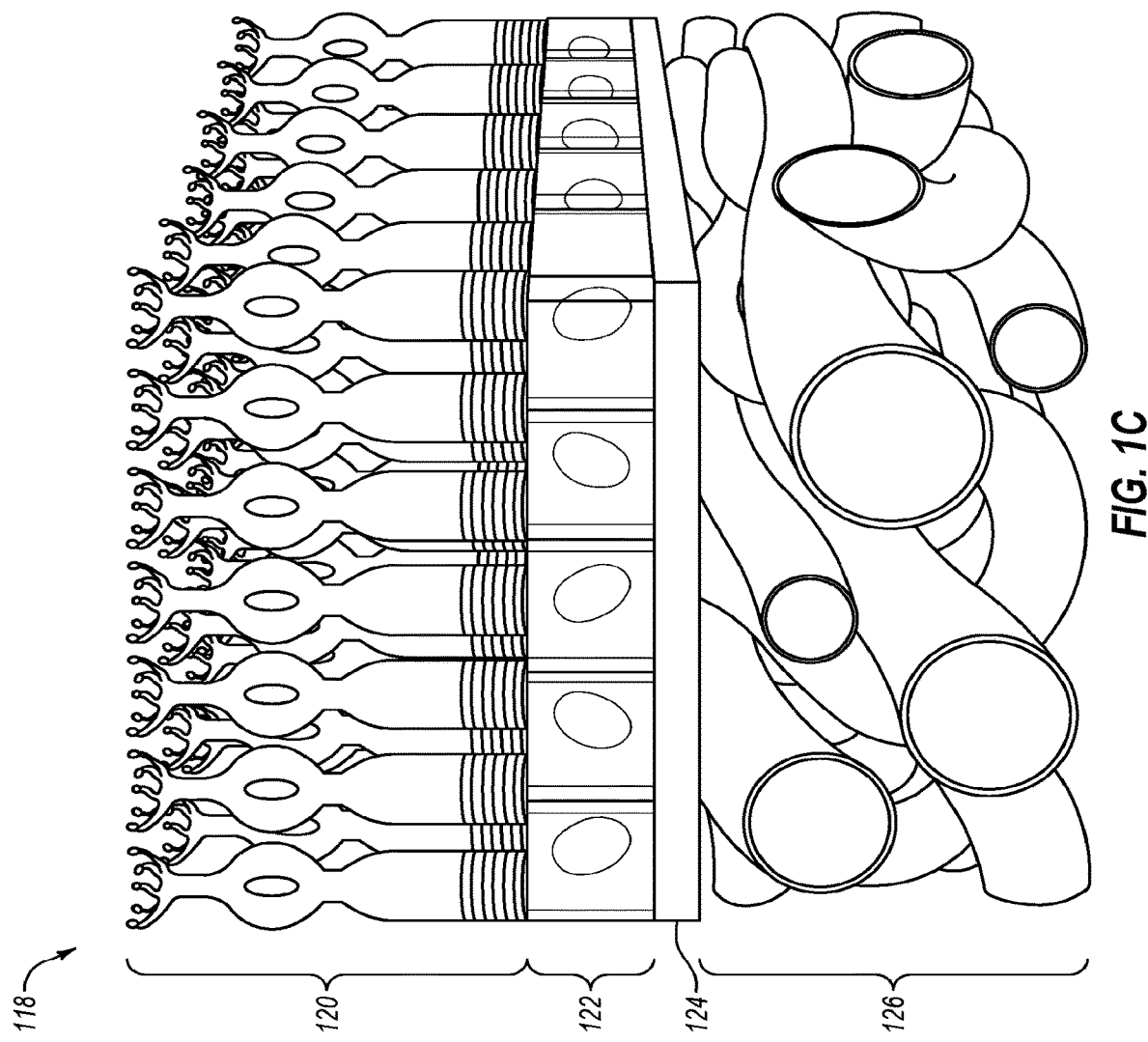
FIG. 1C is a cross-sectional perspective view of a portion of the macula of FIG. 1B.

FIG. 1C is a cross-sectional perspective view of a portion of the macula 118 of FIG. 1B, arranged in accordance with at least one embodiment described herein. FIG. 1C depicts various layers that may make up the macula 118, including photoreceptors 120, retinal pigment epithelial (RPE) cells 122, Bruch's membrane 124, and choroid 126. The macula 118 may have a relatively high concentration of photoreceptors 120 compared to the rest of the retina 112 and without blood vessels, for central and/or high resolution vision. The RPE cells 122 may nourish the photoreceptors 120 by supplying nutrients from the choroid 126 and transporting extracellular material out through the Bruch's membrane 124.

Various conditions may adversely affect vision in the eye 100. For instance, with reference to FIGS. 1A-1C, age-related macular degeneration (AMD) may involve degradation of the RPE cells 122 in the macula 118. In dry AMD, degraded RPE cells 122 may fail to transport extracellular material which may then begin to build up ("Drusen") in between the Bruch's membrane 124 and the RPE cells 122. The Drusen may interfere with the supply of nutrients to the photoreceptors 120, which can lead to vision loss. In wet AMD, new blood vessels (neovascularization) may grow from the choroid 126 and penetrate the Bruch's membrane 124 and the RPE cells 122 to supply nutrients to the photoreceptors 120. The new blood vessels may be weak and prone to bleeding and leakage, which may result in blood and protein leakages, which in turn may damage the photoreceptors 120 and fuel rapid vision loss.

Another condition that may adversely affect vision in the eye 100 may be diabetic macular edema (DME). In more detail, persons with diabetes may experience a slowing of metabolism over time, which may reduce the ability of retinal vessels to deliver enough nutrients, which in turn may induce neovascularization. Fluid leakage from the neovascularization may cause the retina 112 to swell, causing vision loss.

Another condition that may adversely affect vision in the eye 100 may be central serous chorioretinopathy (CSC). In CSC, leakage of fluid accumulates under the central macula 118, resulting in blurred or distorted vision which may progressively decline with each recurrence.

Some embodiments described herein include a laser-based ophthalmological surgical system that includes a therapeutic radiation source configured to emit therapeutic radiation to treat AMD, DME, CSC, and/or other conditions of the eye 100. In general, the therapeutic radiation may be absorbed by RPE cells 122 targeted with the therapeutic radiation. Specifically, the therapeutic radiation may be absorbed by melanin or other chromophore in the RPE cells 122. The absorbed therapeutic radiation may be converted to heat, which may lead to formation of microbubbles in the RPE cells 122. The microbubbles may burst or otherwise destroy RPE cells 122. By targeting degraded RPE cells included in the RPE cells 122, the degraded RPE cells can be destroyed to prevent them from causing further damage.

According to some embodiments, such laser-based ophthalmological surgical systems may use real-time feedback to detect RPE damage and stop therapeutic radiation automatically based on the feedback prior to excessively damaging the targeted RPE cells 122. In an example embodiment, the therapeutic radiation is administered to the targeted RPE cells 122 in pulses with a pulse duration less than or equal to 1.7 microseconds. The administration of the therapeutic radiation may be periodic in some embodiments, with a pulse frequency in a range from 50 hertz (Hz) to 200 Hz (corresponding to a period in a range of 0.02 seconds to 0.005 seconds), such as about 100 Hz (corresponding to a period of 0.01 seconds). For instance, multiple therapeutic radiation pulses, each with a pulse duration of 1.7 microseconds, may be sequentially administered with a pulse frequency of 100 Hz. The administration of pulses may be terminated in response to the feedback indicating occurrence of a maximum exposure to the therapeutic radiation. In other embodiments, the pulse frequency of the therapeutic radiation may be greater than 200 Hz.

The therapeutic radiation may in some embodiments be generally more effective at treating conditions of the eye at higher exposure levels, However, at a particular level of exposure (e.g., power) to the therapeutic radiation, therapeutic radiation may cause excessive damage to the eye that may result in vision loss. To avoid or reduce the likelihood of vision loss due to excessive exposure to the therapeutic radiation while permitting exposure up to a sufficiently high level to be effective, some embodiments described herein may start administration of the therapeutic radiation at a relatively low exposure that ramps up with each successive pulse until real-time feedback indicates a threshold exposure has been reached. In an example, the first pulse of therapeutic radiation may be at about 50% of a relatively high energy level, such as a maximum energy level. More generally, the first pulse may be at a relatively low energy level, and each successively administered pulse of therapeutic radiation may be increased compared to the preceding pulse. The amount of increase from pulse to pulse may be fixed or variable. For instance, in an example embodiment, the amount of increase from pulse to pulse may be fixed at 5% of the relatively high energy level.

The real-time feedback may measure exposure of the targeted RPE cells to the therapeutic radiation by measuring the formation and/or bursting of microbubbles that form on melanosomes of the targeted RPE cells in response to exposure to the therapeutic radiation. In an example embodiment, the formation and/or bursting of the microbubbles may be measured with optical feedback and/or acoustic feedback. In particular, the targeted RPE cells may reflect and/or emit optical and/or acoustic signals or waves that may vary depending on the presence, absence, and/or characteristics (e.g., size, velocity) of the microbubbles. Excessive exposure to the therapeutic radiation after microbubble formation and bursting and RPE damage could damage other retinal structures, which may lead to formation of scotoma on the retina.

Figure 2:
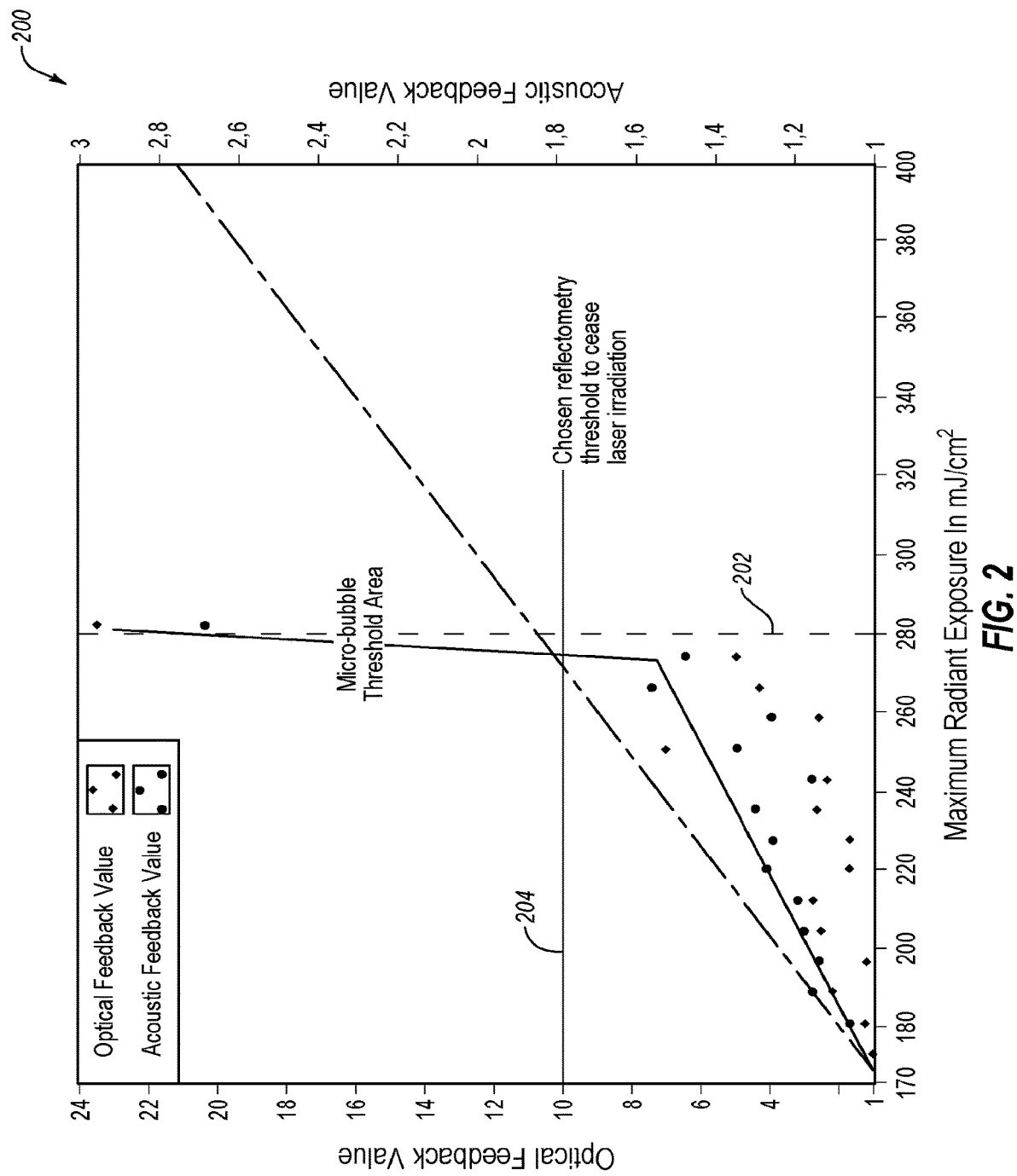
FIG. 2 is a graphical representation of an example feedback response to therapeutic radiation that may be generated by a laser-based ophthalmological surgical system.

FIG. 2 is a graphical representation 200 of an example feedback response to therapeutic radiation that may be generated by a laser-based ophthalmological surgical system, arranged in accordance with at least one embodiment described herein. The horizontal axis is radiant exposure to the therapeutic radiation in millijoules per square centimeter (mJ/cm2), the left vertical axis is optical feedback value in microwatts, and the right axis is acoustic feedback value in millivolts. FIG. 2 includes data points representing the measured optical feedback (diamonds in FIG. 2) and acoustic feedback (circles in FIG. 2) as a function of therapeutic radiation exposure level. Each data point may represent a measurement of the optical or acoustic feedback from the targeted RPE cells and/or from microbubbles thereon after exposure to a pulse of the therapeutic radiation at a corresponding exposure level. All of the optical feedback data points may be collectively referred to as an optical signal and all of the acoustic feedback data points may be collectively referred to as an acoustic signal.

FIG. 2 additionally includes a vertical reference zone 202, at around 280 mJ/cm2 in the example of FIG. 2, that represents a microbubble threshold area at a therapeutic radiation exposure level that may be known or expected to cause excessive damage to the targeted RPE cells. FIG. 2 additionally includes a horizontal reference line 204 at a threshold optical feedback value, at 10 arbitrary units (a.u.) in the example of FIG. 2, which may be selected as an optical feedback value after which irradiation with the therapeutic radiation may be terminated to avoid or reduce the likelihood of excessive damage to the targeted RPE cells.

The optical signal in the example of FIG. 2 may be generated by measuring reflected therapeutic radiation or other reflected radiation from the targeted RPE cells and/or from microbubbles that form thereon.

The acoustic signal in the example of FIG. 2 may be generated by measuring the acoustic response of the targeted RPE cells and/or the microbubbles that form thereon. For instance, as the microbubbles burst after formation, they may emit acoustic waves that may be measured to generate the acoustic signal. As illustrated in FIG. 2, the acoustic signal in this example is somewhat noisy and exhibits substantial fluctuations, particularly around the vertical reference zone 202. This strong fluctuation in the acoustic signal may impose a difficulty in accurately determining when the acoustic signal is at or near a threshold acoustic feedback value indicative of a therapeutic radiation threshold exposure level.

Embodiments described herein may improve the noise level of the acoustic signal. Rather than using an acoustic detector that includes a single ring-shaped piezoelectric transducer to detect the acoustic waves and generate the acoustic signal, embodiments described herein may implement a distributed acoustic detector system that may have a smaller footprint than such a ring-shaped piezoelectric transducer and that may include multiple acoustic detectors that may be spaced apart from each other and electrically separated from each other. In at least one embodiment, the multiple acoustic detectors may be arranged around a circle, optionally at equal angular intervals. The relatively smaller multiple acoustic detectors may be able to respond to acoustic waves faster, may suppress the noise level, and may thus enhance the sensitivity of the distributed acoustic detector system, e.g., compared to the single ring-shaped piezoelectric transducer. Thus, the observed acoustic signal fluctuation illustrated in and described with respect to FIG. 2 may be suppressed.

The distributed acoustic detector system may be operated in a passive detection mode in which acoustic-wave-generating events or features (e.g., microbubble bursting) are measured. Alternatively or additionally, the distributed acoustic detector system may be operated in an active detection mode by emitting interrogation acoustic waves from the distributed acoustic detector system and receiving their reflections at the distributed acoustic detector system to measure structures, events, and/or features which may not emit acoustic waves on their own. The reflected interrogation acoustic waves may be referred to as echo acoustic waves. In these and other embodiments, the distributed acoustic detector system may include multiple acoustic detectors and one or more acoustic signal generators. The acoustic signal generators may emit the interrogation acoustic waves, and the acoustic detectors may receive the echo acoustic waves.

Insofar as the acoustic detectors may be spaced apart from each other, they may be located at different distances from the RPE cells and/or from the microbubbles formed thereon. As such, any acoustic waves emitted or reflected from the RPE cells and/or the microbubbles may reach different acoustic detectors at different times. In these and other embodiments, time difference of arrival of two or more of the received acoustic waves may be used to determine a particular location within an eye of the patient from which the received acoustic waves were emitted and/or reflected.

Figure 3A:
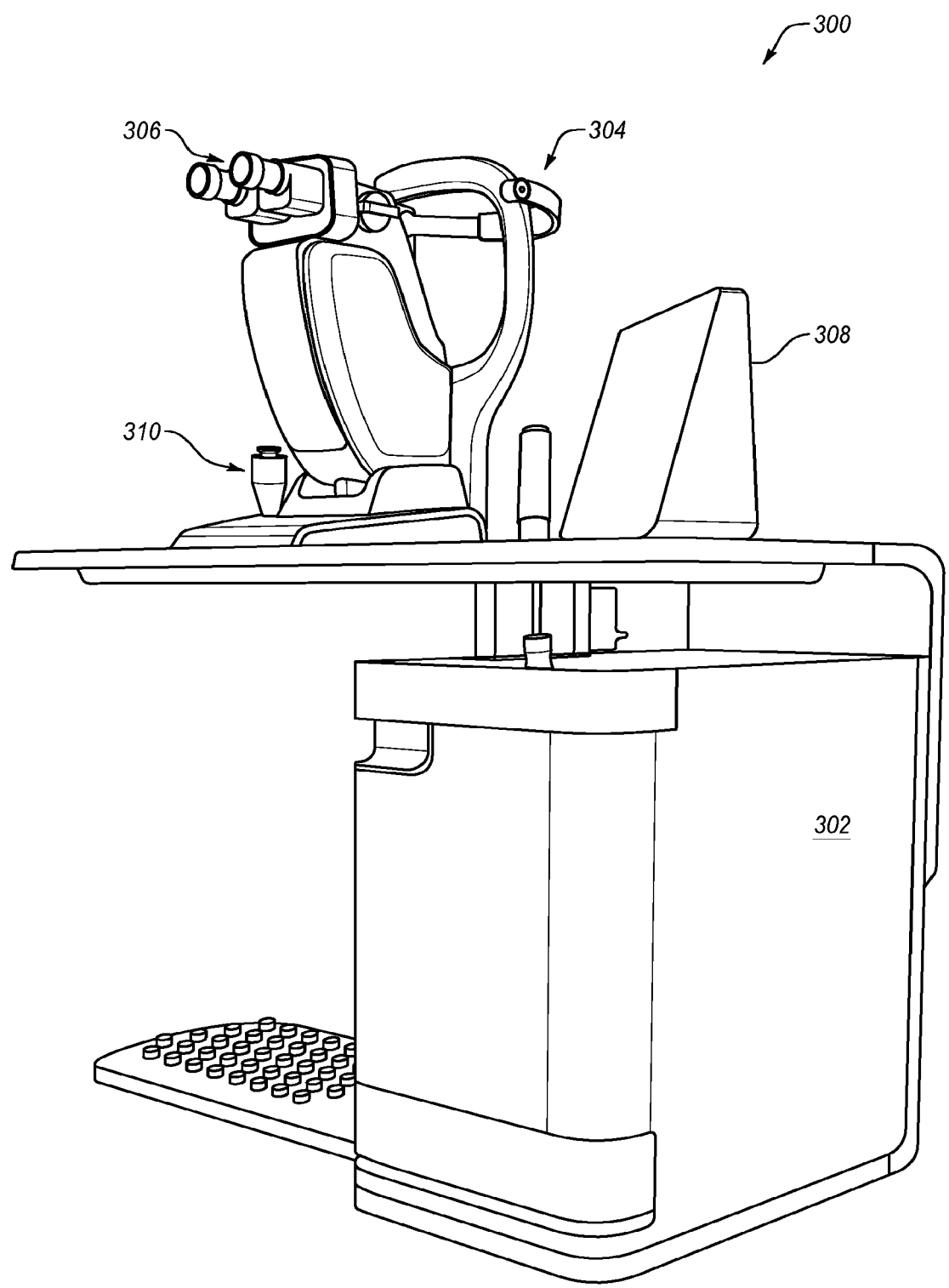
FIG. 3A is a perspective view of an example laser-based ophthalmological surgical system in which a distributed acoustic detector system may be implemented.
Figure 3B:
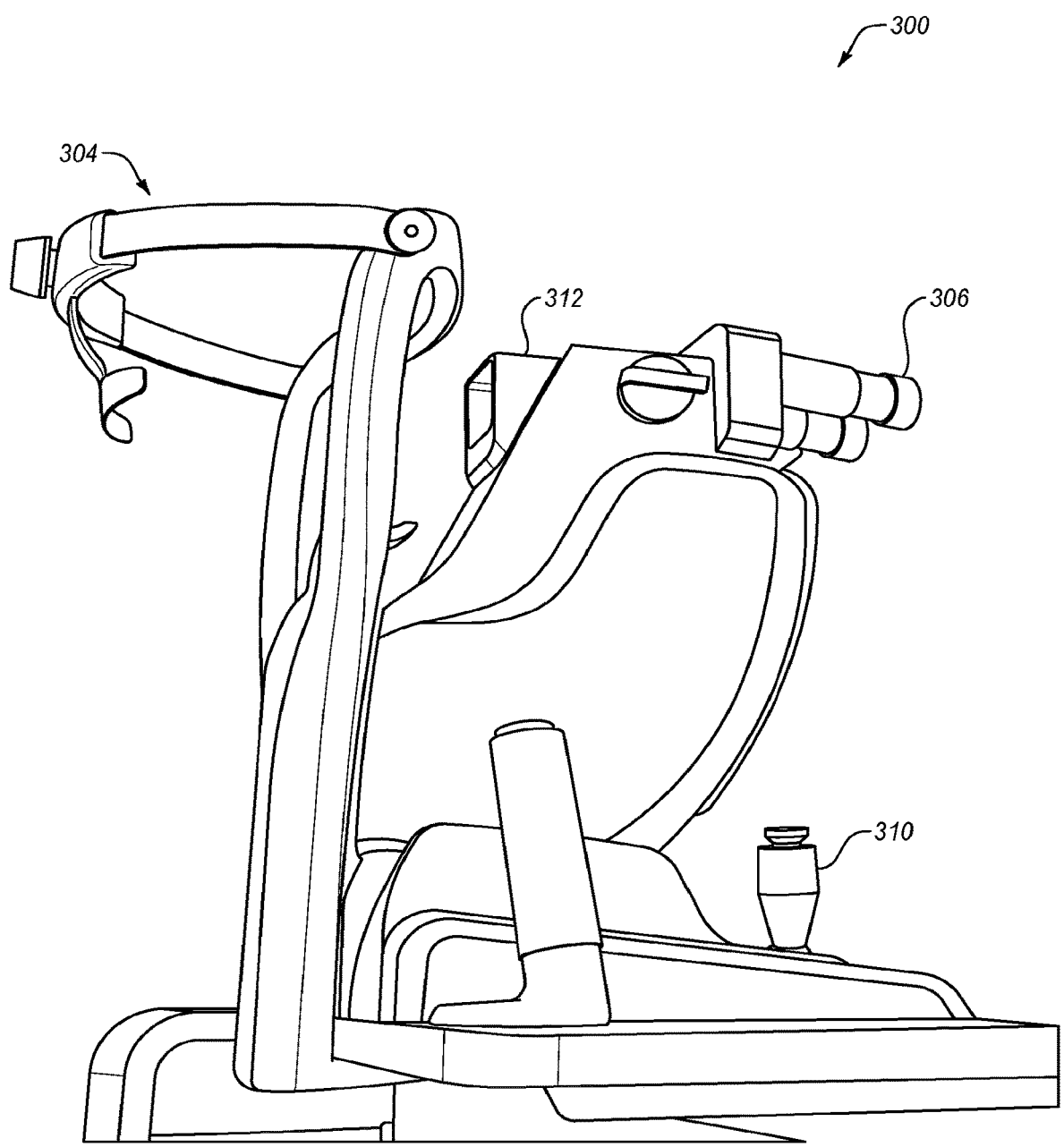
FIG. 3B is a perspective view of a portion of the laser-based ophthalmological system of FIG. 3A.

FIG. 3A is a perspective view of an example laser-based ophthalmological surgical system (hereinafter "system") 300 in which a distributed acoustic detector system may be implemented, arranged in accordance with at least one embodiment described herein. FIG. 3B is a perspective view of a portion of the system 300 of FIG. 3A, arranged in accordance with at least one embodiment described herein. As illustrated, the system 300 may include one or more of a console 302 (FIG. 3A), a head fixation assembly 304, a microscope 306, a graphical user interface (GUI) 308 (FIG.

3A), one or more input devices 310, and a patient contact lens 312 (FIG. 3B) that includes or is coupled to a distributed acoustic detector system.

The console 302 may include a therapeutic radiation source configured to emit therapeutic radiation. The console 302 may also include one or more control systems (e.g., one or more processors, drivers, or other circuits), a cooling system, or other systems or components. The therapeutic radiation emitted by the therapeutic radiation source may have a center wavelength in a range from 500 nanometers (nm) to about 600 nm, such as 527 nm or 577 nm. The therapeutic radiation in some embodiments may be pulsed, meaning the therapeutic radiation source may emit the therapeutic radiation as discrete pulses. The pulses of therapeutic radiation may each have a pulse duration of between half a microsecond to several microseconds, such as 1.7 microseconds, and may be administered periodically in some embodiments, with a pulse frequency in a range of 50 Hz to 200 Hz, such as 100 Hz. As used herein, "pulse frequency" may refer to a frequency at which the discrete pulses of therapeutic radiation are emitted by the therapeutic radiation source, e.g., a repetition rate of the discrete pulses of therapeutic radiation. The pulses of therapeutic radiation may be substantially flat-topped or may have some other shape.

In some embodiments, the therapeutic radiation emitted by the therapeutic radiation source may have up to a maximum energy in a range from 0.5 millijoules (mJ) to 2.0 mJ, such as 1.0 mJ. The therapeutic radiation source may be controlled, e.g., by the control system or other elements of the console 302, to emit discrete pulses of the therapeutic radiation that have an energy per pulse (hereinafter "pulse energy") in a range between 0 mJ up to the maximum energy. For instance, the discrete pulses of therapeutic radiation may be sequentially ramped up beginning at a relatively low pulse energy (e.g., 50% of the maximum energy) and successively ramping up in pulse energy by a fixed or variable amount (e.g., 5% of the maximum energy) until optical and/or acoustic feedback indicates a threshold exposure level of an eye of a patient to the therapeutic radiation has been reached.

The therapeutic radiation may be directed by one or more optical elements from the therapeutic radiation source in the console 302 up to and out through the patient contact lens 312, including through the distributed acoustic detector system, to an eye of a patient during treatment with the eye of the patient. The one or more optical elements may be included in one or more of the console 302, the microscope 306, the patient contact lens 312, and other components of the system 300 and/or may be provided as discrete components within the system 300.

The head fixation assembly 304 may be configured to position and retain a head of the patient during treatment of the eye of the patient with the therapeutic radiation. For instance, the head fixation assembly 304 may be configured to position and retain the head of the patient with the eye of the patient aligned to receive the therapeutic radiation and to the distributed acoustic detector system included in or coupled to the patient contact lens 312.

The microscope 306 may be used by a treatment provider to observe the patient's eye during treatment. Alternatively or additionally, the microscope 306 or other component of the system 300 may include a targeting radiation source that may be optically aligned to target a same location as the therapeutic radiation. The targeting radiation source may emit targeting radiation to identify a specific location within the patient's eye currently targeted to receive therapeutic radiation. In this and other embodiments, the treatment provider may operate the input device 310, the GUI 308, and/or other elements of the system 300 to adjust the particular location within the patient's that is targeted by the targeting radiation and/or the therapeutic radiation.

Figure 4:
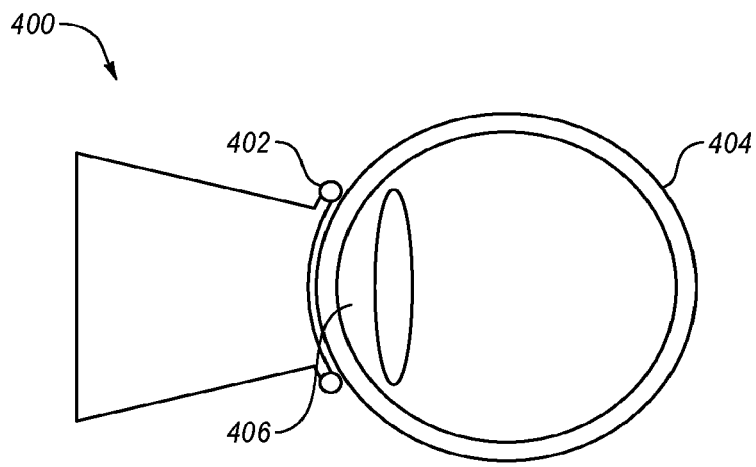
FIG. 4 is a cross-sectional side view of an example patient contact lens that may include a distributed acoustic detector system.

FIG. 4 is a cross-sectional side view of an example patient contact lens 400 that may include a distributed acoustic detector system 402, arranged in accordance with at least one embodiment described herein. The patient contact lens 400 and the distributed acoustic detector system 402 may respectively include or correspond to the patient contact lens 312 and distributed acoustic detector system of FIGS. 3A and 3B.

In general, the distributed acoustic detector system 402 may include a frame structure and multiple acoustic detectors. Each of the acoustic detectors may include a piezoelectric transducer. The frame structure may be configured to be retained in a laser-based ophthalmological surgical system, such as the system 300, proximate to the eye of the patient during therapeutic treatment of the eye of the patient with the laser-based ophthalmological surgical system. The acoustic detectors may be coupled to the frame structure and may be spaced apart from each other and electrically separated from each other.

The frame structure may include a generally circular or ring-shaped portion and the acoustic detectors may be distributed around the circle or ring. In some embodiments, the acoustic detectors may be distributed around the circle or ring of the frame structure at equal or substantially equal angular intervals. Alternatively or additionally, the frame structure may include some or all of the patient contact lens 400.

Alternatively or additionally, the distributed acoustic detector system 402 may include one or more acoustic signal generators. For instance, in embodiments in which the distributed acoustic detector system 402 is configured to detect acoustic waves in the active detection mode, the one or more acoustic signal generators may emit interrogation acoustic waves toward an area of the eye 404 targeted by therapeutic radiation, and one or more of the acoustic detectors may receive echo acoustic waves from the eye 404, and more particularly from the targeted area of the eye 404. Each of the acoustic signal generators may include a piezoelectric transducer.

FIG. 4 additionally illustrates an example alignment of the patient contact lens 400 to an eye 404 of a patient. As illustrated, the eye 404 may generally be aligned to the distributed acoustic detector system 402 with the circle or ring of the frame structure around at least a portion of a cornea 406 of the eye 404.

Figure 5A:
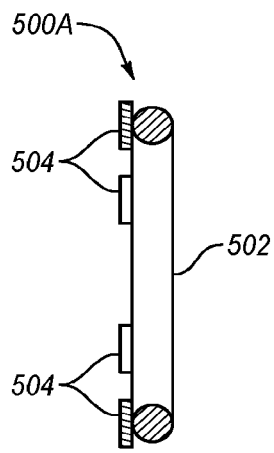
FIGS. 5A and 5B respectively include a cross-sectional side view and a front view of an example distributed acoustic detector system.
Figure 5B:
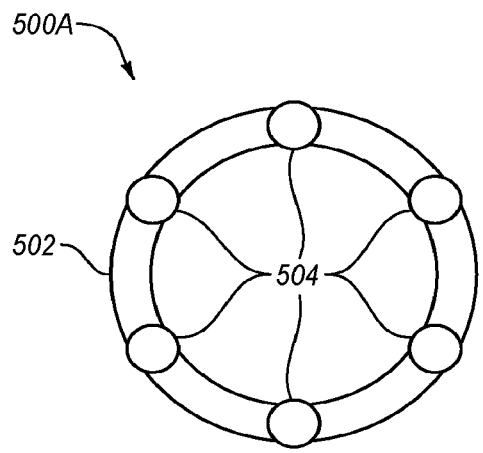

FIGS. 5A and 5B respectively include a cross-sectional side view and a front view of an example distributed acoustic detector system 500A, arranged in accordance with at least one embodiment described herein. The distributed acoustic detector system 500A may include or correspond to one or more of the other distributed acoustic detector systems described herein. The distributed acoustic detector system 500A may include a frame structure 502 and multiple acoustic detectors 504, which may include or correspond to one or more of the other frame structures and acoustic detectors described herein. The distributed acoustic detector system 500A of FIGS. 5A and 5B may be configured to operate in the passive detection mode.

Figure 5C:
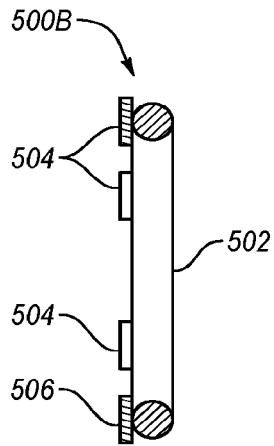
FIGS. 5C and 5D respectively include a cross-sectional side view and a front view of another example distributed acoustic detector system.
Figure 5D:
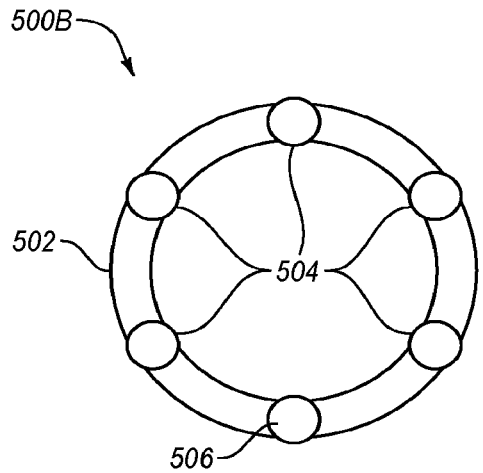

FIGS. 5C and 5D respectively include a cross-sectional side view and a front view of another example distributed acoustic detector system 500B, arranged in accordance with at least one embodiment described herein. The distributed acoustic detector system 500B may include or correspond to one or more of the other distributed acoustic detector systems described herein. The distributed acoustic detector system 500B may include the frame structure 502, multiple acoustic detectors 504, and one or more acoustic signal generators 506, which may include or correspond to one or more of the other frame structures, acoustic detectors, and acoustic signal generators described herein. The distributed acoustic detector system 500B of FIGS. 5C and 5D may be configured to operate in the passive detection mode.

Although a single acoustic signal generator 506 is depicted in FIGS. 5C and 5D, in other embodiments the distributed acoustic detector system 500B may include multiple acoustic signal generators 506. In these and this and other embodiments, the acoustic detectors 504 and acoustic signal generators 506 may be arranged in any suitable arrangement. For instance, the acoustic detectors 504 and the acoustic signal generators 506 may be arranged in an alternating pattern of acoustic detector 504 followed by acoustic signal generator 506, repeating around the frame structure 502. As another example, two acoustic signal generators 506 may be arranged opposite each other on the frame structure 502, e.g., 180 degrees apart, with two acoustic detectors 504 on the frame structure 502 to one side and two acoustic detectors 504 on the frame structure 502 to the other side.

Figure 6A:
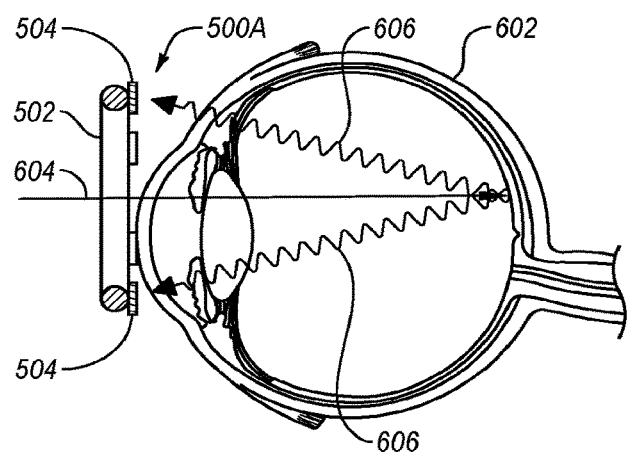
FIGS. 6A and 6B respectively include a cross-sectional side view and a front view of the distributed acoustic detector system of FIGS. 5A and 5B aligned to an eye of a patient.
Figure 6B:
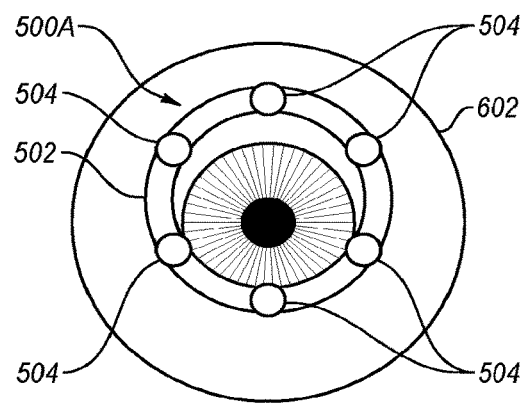
Figure 6C:
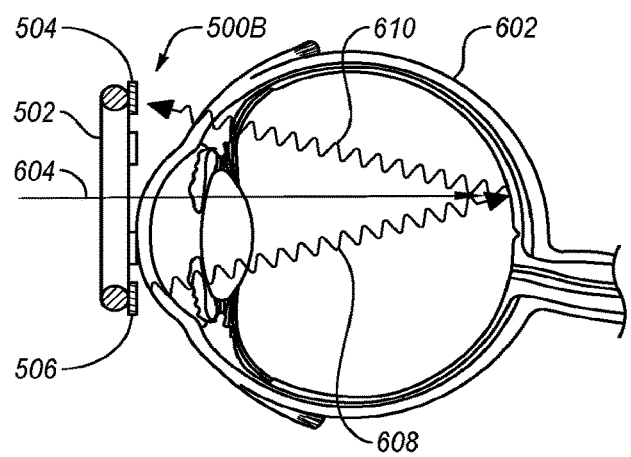
FIGS. 6C and 6D respectively include a cross-sectional side view and a front view of the distributed acoustic detector system of FIGS. 5C and 5D aligned to the eye of the patient.
Figure 6D:
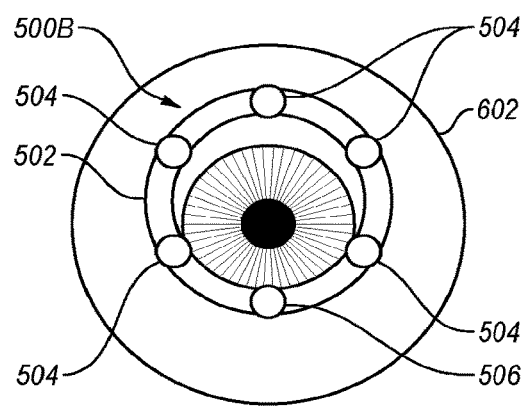

FIGS. 6A and 6B respectively include a cross-sectional side view and a front view of the distributed acoustic detector system 500A of FIGS. 5A and 5B aligned to an eye 602 of a patient, arranged in accordance with at least one embodiment described herein. FIGS. 6C and 6D respectively include a cross-sectional side view and a front view of the distributed acoustic detector system 500B of FIGS. 5C and 5D aligned to the eye 602 of the patient, arranged in accordance with at least one embodiment described herein. As can be seen from a comparison of FIG. 4 to FIGS. 6A-6D, different alignments between a distributed acoustic detector system and an eye of a patient are possible, with the various alignments generally involving a cornea of the eye of the patient being partially or completely surrounded by a circle or ring of a frame structure of the distributed acoustic detector system in some embodiments.

The example of FIG. 6A illustrates the distributed acoustic detector system 500A configured to operate in the passive detection mode in which acoustic-wave-generating events or features, specifically microbubble bursting in this example, may be measured. In these and other embodiments, the eye 602 may be illuminated with therapeutic radiation 604, which may cause microbubbles to form on melanosomes of RPE cells of the eye 602. One or more of the acoustic detectors 504, only two of which are labeled in FIG. 6A for simplicity, may receive acoustic waves 606 from the microbubbles. More particularly, in some embodiments, one or more of the acoustic detectors 504 may receive acoustic waves 606 emitted or generated by bursting of the microbubbles.

The example of FIG. 6C illustrates the distributed acoustic detector system 500B configured to operate in the active detection mode in which interrogation acoustic waves 608 may be generated and emitted by the acoustic signal generator 506, and echo acoustic waves 610 may be received by one or more of the acoustic detectors 504, only one of which is labeled in FIG. 6C for simplicity. The acoustic detectors 504 in this and other embodiments of the distributed acoustic detector systems that include one or more acoustic signal generators may receive, in addition to the echo acoustic waves 610, acoustic waves emitted by the bursting of microbubbles such as the acoustic waves 606 of FIG. 6A.

Figure 7A:
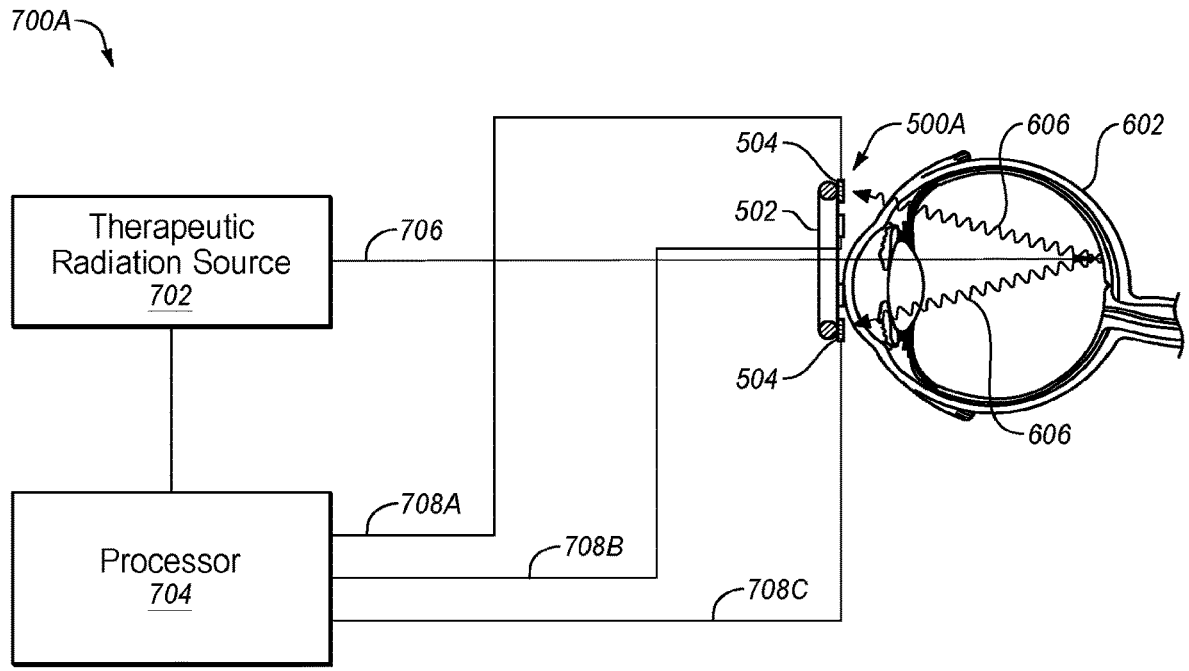
FIGS. 7A and 7B include block diagrams of two example laser-based ophthalmological surgical systems.
Figure 7B:
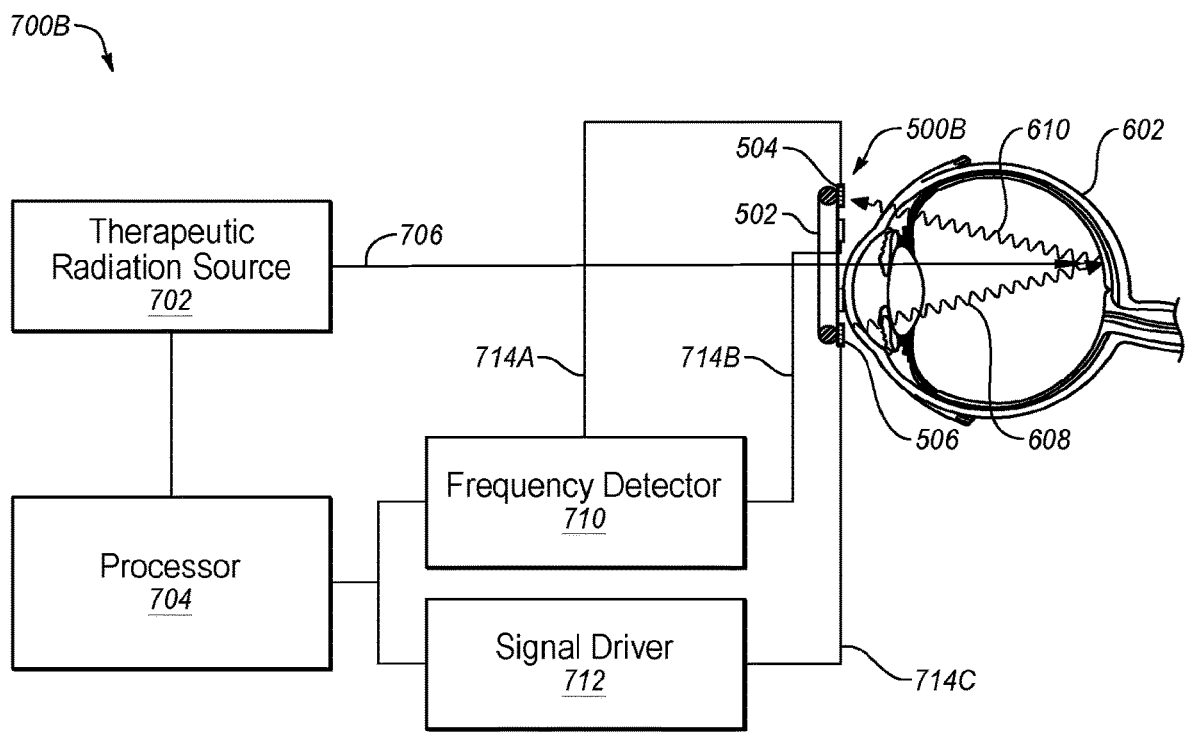

FIGS. 7A and 7B include block diagrams of two example laser-based ophthalmological surgical systems 700A and 700B (hereinafter "system 700A" and "system 700B"), arranged in accordance with at least one embodiment described herein. The system 700A may include one or more of a therapeutic radiation source 702, the distributed acoustic detector system 500A of FIGS. 6A and 6B, and a processor 704. The system 700A may include or correspond to the system 300 of FIGS. 3A and 3B. In these and other embodiments, the system 700A may include one or more other elements not depicted in FIG. 7A for simplicity, such as a head fixation assembly, one or more photodetectors, an imaging system (e.g., microscope), bias and/or modulation circuitry, and/or other elements.

The therapeutic radiation source 702 may be configured to emit therapeutic radiation 706 with a center wavelength in a range from 500 nanometers (nm) to about 600 nm, such as 527 nm or 577 nm. The therapeutic radiation 706 may include or correspond to the therapeutic radiation 604 of FIGS. 6A and 6C. The therapeutic radiation 706 in some embodiments may be pulsed, meaning the therapeutic radiation source 702 may emit the therapeutic radiation 706 as discrete pulses. The pulses of therapeutic radiation 706 may each have a pulse duration of 1.7 microseconds or less, and may be administered periodically in some embodiments, with a pulse frequency in a range of 50 Hz to 200 Hz, such as 100 Hz. As used herein, "pulse frequency" may refer to a frequency at which the discrete pulses of therapeutic radiation 706 are emitted by the therapeutic radiation source 702, e.g., a repetition rate of the discrete pulses of therapeutic radiation 706. The pulses of therapeutic radiation 706 may be substantially flat-topped or may have some other shape.

In some embodiments, the therapeutic radiation 706 emitted by the therapeutic radiation source 702 may have up to a maximum energy in a range from 0.5 millijoules (mJ) to 2.0 mJ, such as 1.0 mJ. The therapeutic radiation source 702 may be controlled to emit discrete pulses of the therapeutic radiation 706 that have an energy per pulse (hereinafter "pulse energy") in a range between 0 mJ up to the maximum energy. For instance, the discrete pulses of therapeutic radiation 706 may be sequentially ramped up beginning at a relatively low pulse energy (e.g., 50% of the maximum energy) and successively ramping up in pulse energy by a fixed or variable amount (e.g., 5% of the maximum energy) until optical and/or acoustic feedback indicates a threshold exposure level of the eye 602 to the therapeutic radiation 706 has been reached.

The processor 704 may be communicatively coupled to one or both of the therapeutic radiation source 702 and the distributed acoustic detector system 500A. In some embodiments, the processor 704 may be communicatively coupled to each of the acoustic detectors 504 individually, as denoted at 708A, 708B, and 708C, to maintain electrical separation of the acoustic detectors 504 from each other.

The processor 704 may be configured to receive detection signals generated by the acoustic detectors 504 and which may be representative of the acoustic waves received by the acoustic detectors 504. For instance, when implemented as piezoelectric transducers, each of the acoustic detectors 504 may output a detection signal with a voltage that varies in accordance with a time-varying pressure exerted on the acoustic detectors 504 by the acoustic waves 606. The processor 704 may determine an exposure level of the eye 602 to the therapeutic radiation 706 based at least in part on one or more detection signals generated by one or more of the acoustic detectors 504. In general, a higher exposure level to—or power of—the therapeutic radiation 706 may cause the formation and bursting of a relatively greater number of microbubbles in the eye 602. The bursting of a relatively greater number of microbubbles in the eye 602 may generate acoustic waves 606 with a relatively greater amplitude, which in turn may be represented by relatively higher voltage or other parameter in the detection signals output by the acoustic detectors 504. Thus, the voltage level or other parameter in the detection signals output by the acoustic detectors 504 may be indicative of the exposure level of the eye 602 to the therapeutic radiation 706 and/or may be used to determine the exposure level of the eye 602 to the therapeutic radiation 706.

The processor 704 may also be configured to control the therapeutic radiation source 702 and/or other circuitry that drives or otherwise operates the therapeutic radiation source 702. Accordingly, the processor 704 may be configured to terminate exposure of the eye 602 to the therapeutic radiation 706 in response to the exposure level of the eye 602 reaching a threshold exposure level. For instance, in response to the exposure level of the eye 602 reaching the threshold exposure level, the processor 704 may be configured to turn off or otherwise terminate operation of the therapeutic radiation source 702.

The acoustic waves 606 may reach the acoustic detectors 504 at different times, depending on a distance between a given one of the acoustic detectors 504 and a target location of the eye 602 at which the therapeutic radiation 706 is targeted. In these and other embodiments, multiple detection signals generated by acoustic detectors 504 may be used to determine a particular location within the eye 602 at which one or more microbubbles form and burst, as described in more detail with respect to FIG. 8A.

Figure 8A:
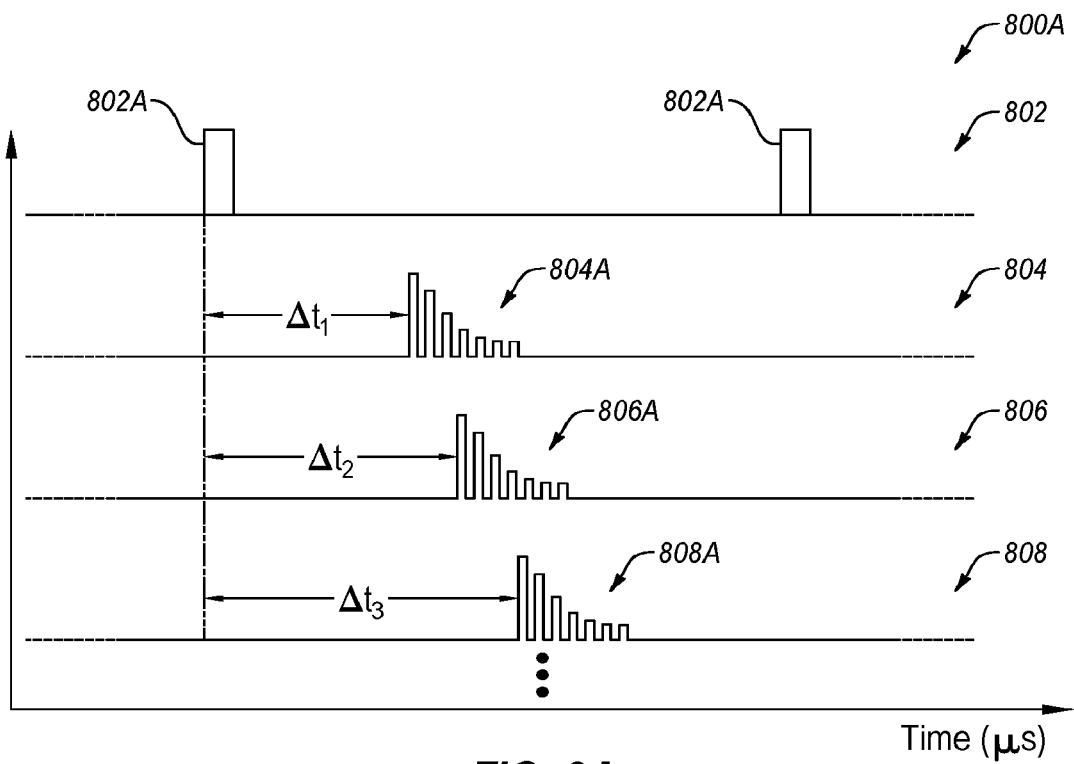
FIG. 8A is a graphical representation of example therapeutic radiation and detection signals.

FIG. 8A is a graphical representation of example therapeutic radiation 802 and detection signals 804, 806, and 808, arranged in accordance with at least one embodiment described herein. The therapeutic radiation 802 may include or correspond to the therapeutic radiation 706 of FIG. 7A and/or other therapeutic radiation described herein. The detection signals 804, 806, and 808 may be generated by acoustic detectors, such as the acoustic detectors 504 of the distributed acoustic detector system 500A.

As illustrated in FIG. 8A, the therapeutic radiation 802 includes discrete pulses 802A. The discrete pulses 802A may have a pulse duration in a range less than or equal to 1.7 microseconds. The therapeutic radiation 802 may be modulated to include the discrete pulses 802A at a pulse repetition rate, which may be in a range from, e.g., 50 Hz to 200 Hz, such as 100 Hz. Each of the discrete pulses 802A of the therapeutic radiation 802 may cause the formation and bursting of microbubbles.

Each of the detection signals 804, 806, 808 may include one or more pulses or pulse trains 804A, 806A, or 808A generated when acoustic waves emitted by the bursting of the microbubbles responsive to illumination with the therapeutic radiation 802 reach the corresponding acoustic detector. The acoustic detectors that generate the detection signals 804, 806, 808 may be located different distances from a target location of an eye at which the therapeutic radiation 802 is targeted. For instance, a first acoustic detector that generates the detection signal 804 may be closest to the target location, a second acoustic detector that generates the detection signal 806 may be a relatively greater distance from the target location, and a third acoustic detector that generates the detection signal 808 may be a relatively still greater distance from the target location.

A time delay $\Delta t1$, $\Delta t2$, or $\Delta t3$ between the start of each of the discrete pulses 802A in the therapeutic radiation and a start of each of the pulses or pulse trains 804A, 806A, or 808A in each of the detection signals 804, 806, 808 may depend on the corresponding distance between the target location of the eye at which the therapeutic radiation 802 is targeted and the corresponding first, second, or third acoustic detector. For instance, a given acoustic wave emitted when one or more microbubbles burst may take longer to travel greater distances, such that the acoustic wave may reach the first acoustic detector first, followed by the second acoustic detector, followed by the third acoustic detector. With combined reference to FIGS. 7A and 8A, the processor 704 may be configured to determine a particular location, e.g., a target location, within the eye 602 at which the one or more microbubbles form and burst based on a time difference of arrival (e.g., based on at least $\Delta t2-\Delta t1$ and $\Delta t3-\Delta t1$) of the acoustic wave. In this and other embodiments, the processor 704 may indirectly determine the time differences of arrival by measuring each of the time delays $\Delta t1$, $\Delta t2$, and $\Delta t3$ and then calculating $\Delta t2-\Delta t1$ and $\Delta t3-\Delta t1$. Alternatively or additionally, the processor 704 may directly determine the time differences of arrival by measuring, e.g., a first time difference of arrival between the pulse or pulse train 804A and the pulse or pulse train 806A and a second time difference of arrival between the pulse or pulse train 804A and the pulse or pulse train 808A.

Referring to FIG. 7B, the system 700B may include one or more of the therapeutic radiation source 702, the distributed acoustic detector system 500B of FIGS. 6C and 6D, the processor 704, a frequency detector 710, and a signal driver 712. The system 700B may include or correspond to the system 300 of FIGS. 3A and 3B. In these and other embodiments, the system 700B may include one or more other elements not depicted in FIG. 7B for simplicity, such as a head fixation assembly, one or more photodetectors, an imaging system (e.g., microscope), bias and/or modulation circuitry, and/or other elements.

In the system 700B of FIG. 7B, the processor 704, the frequency detector 710, and/or the signal driver 712 may be communicatively coupled to one or both of the therapeutic radiation source 702 and the distributed acoustic detector system 500B. In some embodiments, the frequency detector 710 may be communicatively coupled to each of the acoustic detectors 504 individually and the signal driver 712 may be communicatively coupled to each of the acoustic signal generators 506 individually, as denoted at 714A, 714B, and 714C, to maintain electrical separation of the acoustic detectors 504 and/or the acoustic signal generator 506 from each other.

The signal driver 712 may be communicatively coupled to the acoustic signal generator 506. The signal driver 712 may be configured to drive the acoustic signal generator 506 to generate and emit interrogation acoustic waves. In embodiments in which the distributed acoustic detector system 500B includes multiple acoustic signal generators 506, the signal driver 712 may drive the multiple acoustic signal generators to generate and emit interrogation acoustic waves that constructively combine along a preferred direction toward the target location at which the therapeutic radiation 706 is targeted.

The processor 704 may be configured to receive detection signals generated by the acoustic detectors 504 and which may be representative of the acoustic waves received by the acoustic detectors 504. The detection signals may be received at the processor 704 before or after passing through the frequency detector 710. The acoustic waves received by the acoustic detectors 504 in the example of FIG. 7B may include echo acoustic waves that include reflections of the interrogation acoustic waves from microbubbles that form and/or burst in the eye 602 and acoustic waves emitted by bursting of the microbubbles.

As in the system 700A of FIG. 7A, in the system 700B of FIG. 7B, the processor 704 may determine an exposure level of the eye 602 to the therapeutic radiation 706 based at least in part on one or more detection signals generated by the acoustic detectors 504. Alternatively or additionally, the processor 704 may be configured to terminate exposure of the eye 602 to the therapeutic radiation 706 in response to the exposure level of the eye 602 reaching a threshold exposure level. Alternatively or additionally, the processor 704 may be configured to determine a particular location, e.g., a target location, within the eye 602 at which the one or more microbubbles form and burst based on a time difference of arrival of a detected echo acoustic wave at each of the acoustic detectors 504.

Figure 8B:
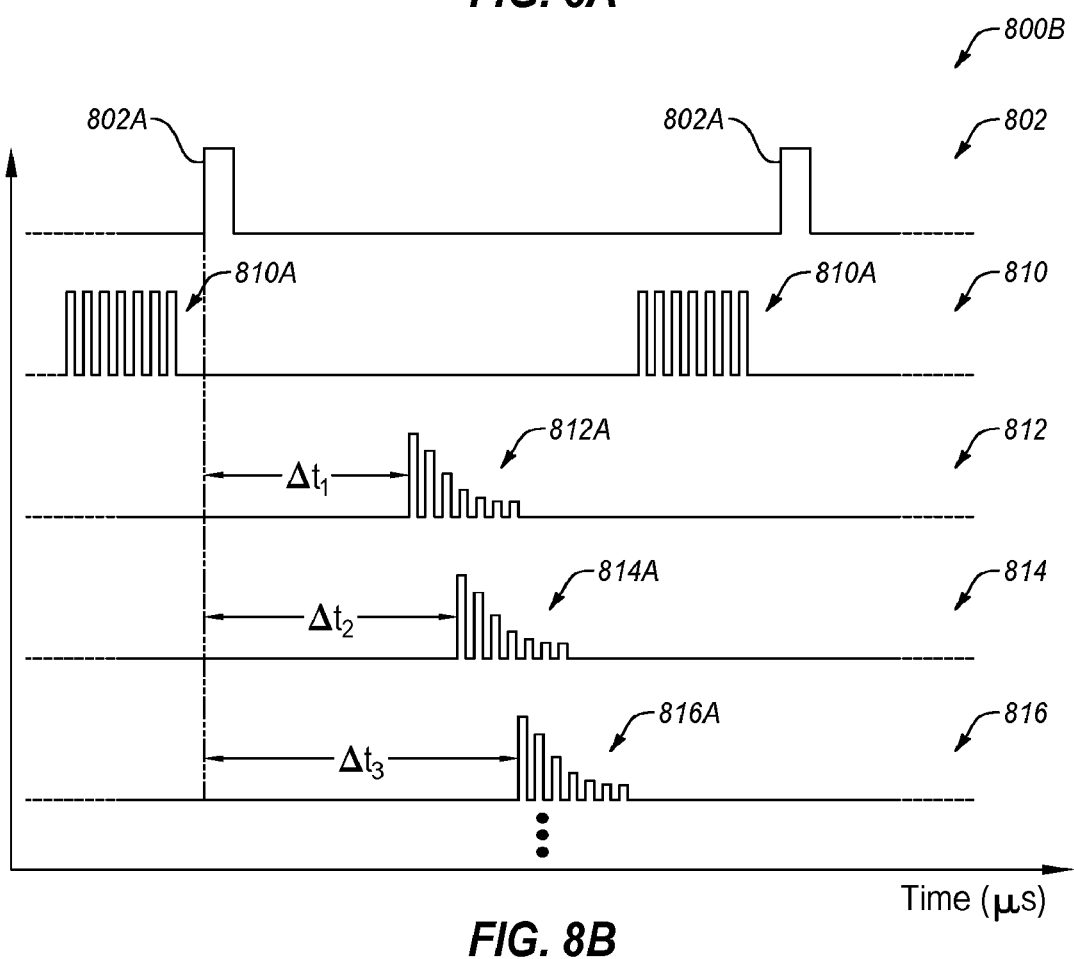
FIG. 8B is a graphical representation of the therapeutic radiation of FIG. 8A, an acoustic signal generator driver signal, and detection signals.

FIG. 8B is a graphical representation of the therapeutic radiation 802 of FIG. 8A, an acoustic signal generator driver signal 810 (hereinafter "driver signal 810"), and detection signals 812, 814, and 816, arranged in accordance with at least one embodiment described herein. The driver signal 810 may be provided to one or more acoustic signal generators, such as the acoustic signal generator 506 of the distributed acoustic detector system 500B, to cause the acoustic signal generators to emit interrogation acoustic waves. The detection signals 812, 814, and 816 may be generated by acoustic detectors, such as the acoustic detectors 504 of the distributed acoustic detector system 500B, responsive to echo acoustic waves that arrive at and are measured by the acoustic detectors.

The driver signal 810 may include one or more pulses or pulse trains 810A. In particular, in the example of FIG. 8B, the driver signal 810 includes pulse trains 810A, each with a pulse train duration that may be on the order of an expected duration of microbubble formation and bursting. Each of the pulse trains 810A of the driver signal 810 may cause an acoustic signal generator to generate and emit a corresponding train of interrogation acoustic waves with a same or similar train duration as the pulse trains 810A. In an example embodiment, the pulse train duration of each of the pulse trains 810A of the driver signal 810, and the train duration of each of the trains of interrogation acoustic waves, may be in a range from four to sixteen microseconds. The timing of the pulse trains 810A relative to the discrete pulses 802A when emitted by a therapeutic radiation source may be configured to cause each of the corresponding trains of interrogation acoustic waves to reach a target location of an eye at the same time or about the same time as a corresponding one of the discrete pulses 802A of the therapeutic radiation 802. The target location may then be exposed to each of the trains of interrogation acoustic waves for the train duration, which may be on the order of the expected duration of microbubble formation and bursting.

Each of the trains of interrogation acoustic waves may be reflected from the target location as a train of echo acoustic waves with parameters such as Doppler (frequency) shift, amplitude, and/or other parameters that may be representative of microbubble size and surface motion at the target location. Each of the trains of echo acoustic waves may be represented as a pulse or pulse train 812A, 814A, or 816A in the corresponding detection signal 812, 814, or 816.

With combined reference to FIGS. 7B and 8B, in this and other embodiments, the processor 704 may be configured to analyze the detection signals 812, 814, 816, each representative of one or more detected echo acoustic waves, such as a train of echo acoustic waves, to determine a particular location within the eye 602 at which one or more microbubbles formed based on a time difference of arrival of the one or more detected echo acoustic waves at the detectors 504 of the distributed acoustic detector system 500B. For instance, the processor 704 may measure each of time delays $\Delta t1$, $\Delta t2$, and $\Delta t3$ denoted in FIG. 8B and then may calculate $\Delta t2 - \Delta t1$ and $\Delta t3 - \Delta t1$. Alternatively or additionally, the processor 704 may directly determine the time differences of arrival by measuring, e.g., a first time difference of arrival between the pulse train 812A and the pulse train 814A and a second time difference of arrival between the pulse train 812A and the pulse train 816A. From the time differences of arrival and/or other information, the particular location within the eye 602 at which the one or more microbubbles formed may be determined.

Referring to FIG. 7B, the frequency detector 710 may be communicatively coupled to each of the acoustic detectors 504 of the distributed acoustic detector system 500B. The frequency detector 710 may be configured to determine frequencies of detected echo acoustic waves over time. The processor 704 may be configured to determine at least one time at which the microbubbles form and/or burst based on frequencies of the detected echo acoustic waves as a function of time.

Frequencies of the echo acoustic waves may differ from that of the interrogation acoustic waves, depending on surface motion of the microbubbles. The frequency difference, also referred to as Doppler shift or frequency shift, may be at least several kilohertz (kHz) up to one megahertz (MHz) or more.

The frequency detector 710 may be configured to determine the frequency difference between the interrogation acoustic waves and the echo acoustic waves. As microbubbles grow, the echo acoustic waves may shift to shorter wavelength (higher frequency) compared to the interrogation acoustic waves. In more detail, as the microbubbles form, they may expand at a rate on the order of sub microseconds. As such, walls of the expanding microbubbles may move at speeds on the order of meters per second. The Doppler shift may be a few percentage of the interrogation acoustic waves. For instance, if the interrogation acoustic waves have a frequency of one MHz, the Doppler shift may be about 10 kHz.

However, when microbubbles burst, the echo acoustic waves may abruptly shift to longer wavelength (lower frequency) compared to the interrogation acoustic waves with the walls of the bursting microbubbles moving on the order of 10 to 100 times faster than during expansion. The Doppler shift during bursting may vary accordingly. Thus, the processor 704 may be configured to determine at least one time at which the microbubbles form and/or burst based on frequencies of the detected echo acoustic waves over time.

The frequency detector 710 may include a heterodyne frequency modulation (FM) receiver, a digital electronic circuit, or other suitable frequency detector. When implemented as a digital electronic circuit, the frequency detector 710 may include a field programmable gate array (FPGA), a digital signal processor (DSP), an application specific integrated circuit (ASIC), or other suitable digital electronic circuit. Such a digital electronic circuit may be configured to determine frequencies of detected echo acoustic waves over time by applying a Fourier transform to digitized detection signals.

Figure 9:
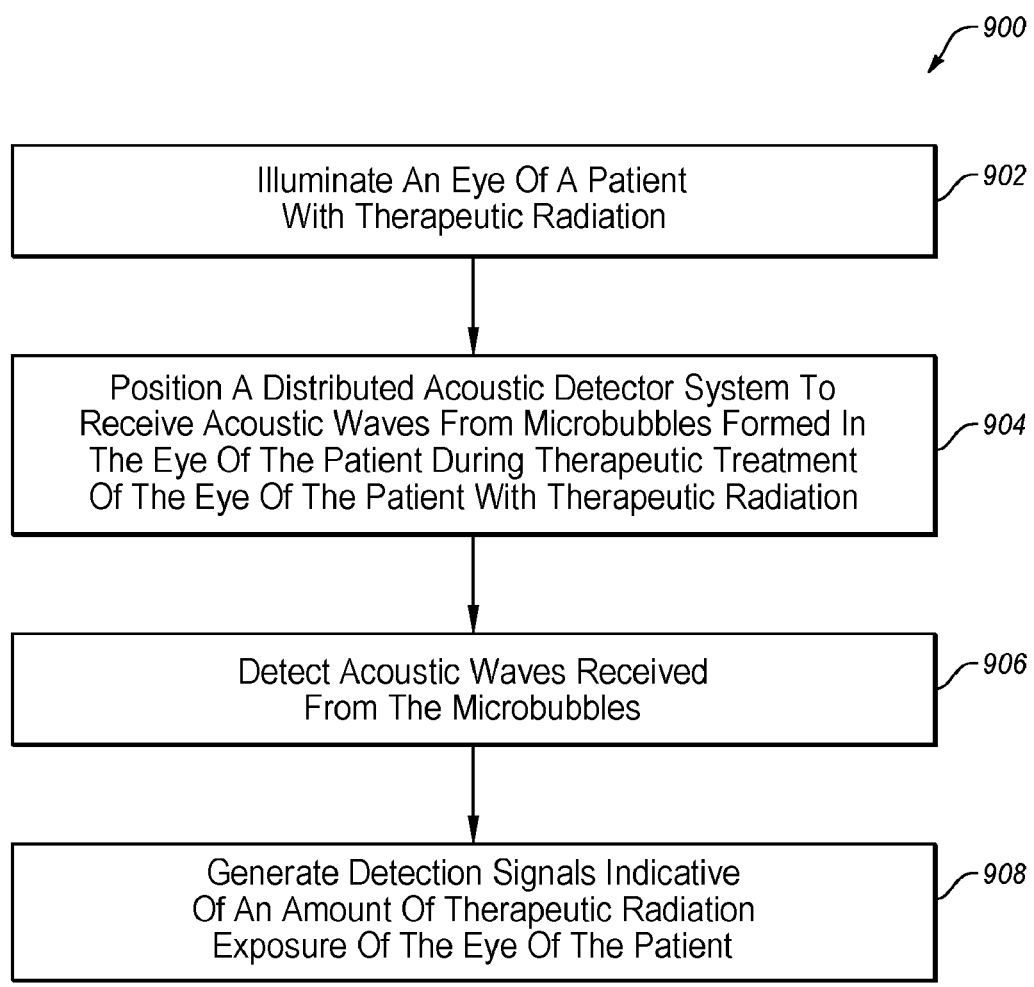
FIG. 9 illustrates a flow diagram of an example method of therapeutic radiation dosimetry.

FIG. 9 illustrates a flow diagram of an example method 900 of therapeutic radiation dosimetry, arranged in accordance with at least some embodiments described herein. The method 900 may be performed, in whole or in part, by one or more of the systems 300, 700A, 700B, one or more of the distributed acoustic detector systems 402, 500A, 500B, and/or in one or more other laser-based ophthalmological surgical systems, distributed acoustic detector systems, other suitable systems. Alternatively or additionally, the method 900 may be implemented by a processor that performs or controls performance of one or more of the operations of the method 900. For instance, a computer (such as the computing device 1000 of FIG. 10) or other processor may be included in the system 300, 700A, or 700B and/or may be communicatively coupled to the distributed acoustic detector system 402, 500A, or 500B and may execute software or other computer-readable instructions accessible to the computer, e.g., stored on a non-transitory computer-readable medium accessible to the computer, to perform or control the system 300, 700A, or 700B or the distributed acoustic detector system 402, 500A, or 500B to perform the method 900 of FIG. 9.

The method 900 may include one or more of blocks 902, 904, 906, and/or 908. Although illustrated as discrete blocks, various blocks may be divided into additional blocks, supplemented with additional blocks, combined into fewer blocks, or eliminated, depending on the particular implementation. The method 900 may begin at block 902.

In block 902 ("Illuminate An Eye Of A Patient With Therapeutic Radiation"), an eye of a patient may be illuminated with therapeutic radiation. The therapeutic radiation may cause microbubbles to form on melanosomes of RPE cells of the eye of the patient during therapeutic treatment of the eye of the patient. The therapeutic radiation may include, e.g., the therapeutic radiation 604 or 706 of FIGS. 6A, 6C, 7A, and/or 7B. Block 902 may be followed by block 904.

In block 904 ("Position A Distributed Acoustic Detector System To Receive Acoustic Waves From Microbubbles Formed In The Eye Of The Patient During Therapeutic Treatment Of The Eye Of The Patient With Therapeutic Radiation"), a distributed acoustic detector system may be positioned to receive acoustic waves from the microbubbles formed in the eye of the patient during the therapeutic treatment of the eye of the patient with the therapeutic radiation. The distributed acoustic detector system may be positioned to receive the acoustic waves prior to illuminating the eye of the patient with the therapeutic radiation. The distributed acoustic detector system may include, e.g., the distributed acoustic detector system 402, 500A, or 500B described herein. Block 904 may be followed by block 906.

In block 906 ("Detect Acoustic Waves Received From The Microbubbles"), acoustic detectors of the distributed acoustic detector system may detect the acoustic waves received from the microbubbles formed in the eye of the patient. The received acoustic waves may include acoustic waves generated and emitted when the microbubbles burst and/or echo acoustic waves, e.g., reflections of interrogation acoustic waves, reflected back from the microbubbles. Thus, detecting the acoustic waves may include detecting acoustic waves emitted by bursting of the microbubbles in at least one embodiment. The acoustic detectors detecting the acoustic waves may include the acoustic detectors receiving the acoustic waves at sufficient strength to elicit a response in the acoustic detectors. Block 906 may be followed by block 908.

In block 908 ("Generate Detection Signals Indicative Of An Amount Of Therapeutic Radiation Exposure Of The Eye Of The Patient"), the acoustic detectors may generate detection signals that are indicative of an amount of therapeutic radiation exposure of the eye of the patient. The detection signals may include electrical signals generated by the acoustic detectors and that are representative of the detected acoustic waves. As described elsewhere, a voltage level or other parameter in the detection signals may indicate an exposure level of the eye of the patient to the therapeutic radiation.

For this and other procedures and methods disclosed herein, the functions or operations performed in the processes and methods may be implemented in differing order. Furthermore, the outlined operations are only provided as examples, and some of the operations may be optional, combined into fewer operations, supplemented with other operations, or expanded into additional operations without detracting from the disclosed embodiments.

For instance, the method 900 may further include analyzing the detection signals generated by the acoustic detectors and each representative of a detected acoustic wave to determine a particular location within the eye of the patient at which a microbubble formed and burst based on a time difference of arrival of the detected acoustic wave at the acoustic detectors.

Alternatively or additionally, the method 900 may further include controlling the distributed acoustic detector system to emit interrogation acoustic waves from at least one acoustic signal generator into the eye of the patient. In this and other embodiments, detecting the acoustic waves may include detecting echo acoustic waves that include reflections of the interrogation acoustic waves from the microbubbles. Alternatively or additionally, the method 900 may further include analyzing the detection signals generated by the acoustic detectors and each representative of a detected echo acoustic wave to determine a particular location within the eye of the patient at which a microbubble formed and burst based on a time difference of arrival of the detected echo acoustic wave at the acoustic detectors.

Alternatively or additionally, the method 900 may further include determining frequencies of detected echo acoustic waves over time and determining at least one time at which the microbubbles form or burst based on frequencies of the detected echo acoustic waves as a function of time.

Alternatively or additionally, the method 900 may further include digitizing each of the detection signals. In this and other embodiments, determining frequencies of the detected echo acoustic waves may include performing a Fourier transform of each of the digitized detection signals.

Alternatively or additionally, the method 900 may further include determining an exposure level of the eye of the patient to the therapeutic radiation based at least in part on one or more detection signals generated by one or more of the acoustic detectors. The method 900 may further include terminating exposure of the eye of the patient to the therapeutic radiation emitted by the therapeutic radiation source in response to the exposure level of the eye of the patient to the therapeutic radiation reaching a threshold exposure level.

Figure 10:
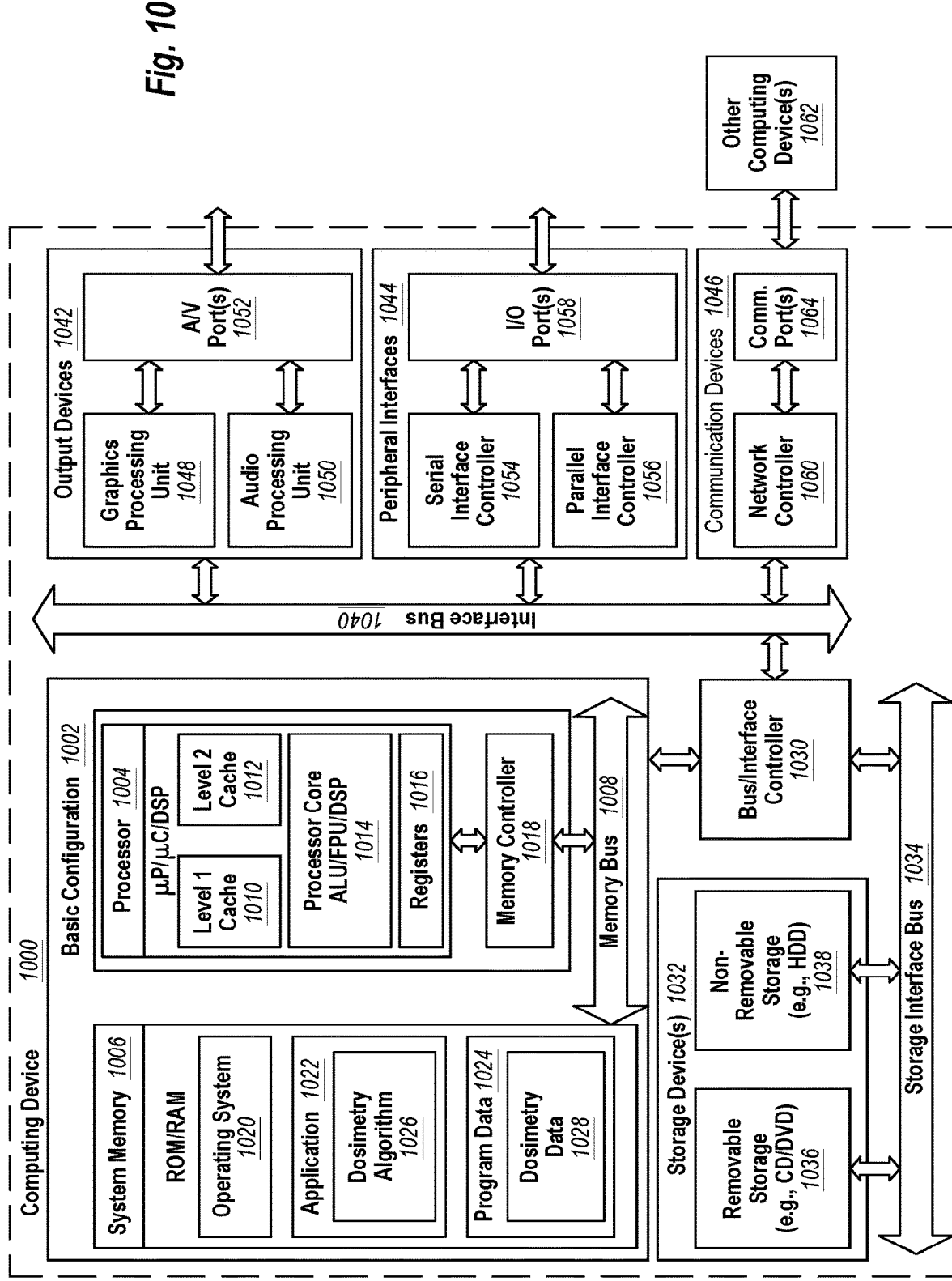
FIG. 10 illustrates a block diagram of an example computing device, all arranged in accordance with at least one embodiment of the present disclosure.

FIG. 10 illustrates a block diagram of an example computing device 1000, in accordance with at least one embodiment of the present disclosure. The computing device 1000 may be used in some embodiments to perform or control performance of one or more of the methods and/or operations described herein. For instance, the computing device may be communicatively coupled to and/or included in the systems 300, 700A, 700B and/or the distributed acoustic detector systems 402, 500A, 500B to perform or control performance of the method 900 of FIG. 9. In a basic configuration 1002, the computing device 1000 typically includes one or more processors 1004 and a system memory 1006. A memory bus 1008 may be used for communicating between the processor 1004 and the system memory 1006.

Depending on the desired configuration, the processor 1004 may be of any type including, such as a microprocessor (µP), a microcontroller (µC), a digital signal processor (DSP), or any combination thereof. The processor 1004 may include one or more levels of caching, such as a level one cache 1010 and a level two cache 1012, a processor core 1014, and registers 1016. The processor core 1014 may include an arithmetic logic unit (ALU), a floating point unit (FPU), a digital signal processing core (DSP Core), or any combination thereof. An example memory controller 1018 may also be used with the processor 1004, or in some implementations, the memory controller 1018 may be an internal part of the processor 1004.

Depending on the desired configuration, the system memory 1006 may be of any type, such as volatile memory (such as RAM), non-volatile memory (such as ROM, flash memory, or the like), or any combination thereof. The system memory 1006 may include an operating system 1020, one or more applications 1022, and program data 1024. The application 1022 may include a dosimetry algorithm 1026 that is arranged to measure therapeutic radiation dosimetry. The program data 1024 may include dosimetry data 1028 such as values included in or derived from detection signals generated by acoustic detectors and/or a table, formula(s), or other information that relates such values to therapeutic radiation exposure levels. In some embodiments, the application 1022 may be arranged to operate with the program data 1024 on the operating system 1020 to perform one or more of the methods and/or operations described herein, including those described with respect to FIG. 9.

The computing device 1000 may include additional features or functionality, and additional interfaces to facilitate communications between the basic configuration 1002 and any other devices and interfaces. For example, a bus/interface controller 1030 may be used to facilitate communications between the basic configuration 1002 and one or more data storage devices 1032 via a storage interface bus 1034. The data storage devices 1032 may include removable storage devices 1036, non-removable storage devices 1038, or a combination thereof. Examples of removable storage and non-removable storage devices include magnetic disk devices such as flexible disk drives and hard-disk drives (HDDs), optical disk drives such as compact disk (CD) drives or digital versatile disk (DVD) drives, solid state drives (SSDs), and tape drives to name a few. Example computer storage media may include volatile and non-volatile, removable and non-removable media implemented in any method or technology for storage of information, such as computer-readable instructions, data structures, program modules, or other data.

The system memory 1006, the removable storage devices 1036, and the non-removable storage devices 1038 are examples of computer storage media. Computer storage media includes, but is not limited to, RAM, ROM, EEPROM, flash memory or other memory technology, CD-ROM, digital versatile disks (DVDs) or other optical storage, magnetic cassettes, magnetic tape, magnetic disk storage or other magnetic storage devices, or any other medium which may be used to store the desired information and which may be accessed by the computing device 1000. Any such computer storage media may be part of the computing device 1000.

The computing device 1000 may also include an interface bus 1040 for facilitating communication from various interface devices (e.g., output devices 1042, peripheral interfaces 1044, and communication devices 1046) to the basic configuration 1002 via the bus/interface controller 1030. The output devices 1042 include a graphics processing unit 1048 and an audio processing unit 1050, which may be configured to communicate to various external devices such as a display or speakers via one or more A/V ports 1052. The peripheral interfaces 1044 include a serial interface controller 1054 or a parallel interface controller 1056, which may be configured to communicate with external devices such as input devices (e.g., keyboard, mouse, pen, voice input device, touch input device, and/or others), sensors, or other peripheral devices (e.g., printer, scanner, and/or others) via one or more I/O ports 1058. The communication devices 1046 include a network controller 1060, which may be arranged to facilitate communications with one or more other computing devices 1062 over a network communication link via one or more communication ports 1064.

The network communication link may be one example of a communication media. Communication media may typically be embodied by computer-readable instructions, data structures, program modules, or other data in a modulated data signal, such as a carrier wave or other transport mechanism, and may include any information delivery media. A "modulated data signal" may be a signal that includes one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR), and other wireless media. The term "computer-readable media" as used herein may include both storage media and communication media.

The computing device 1000 may be implemented as a portion of a small-form factor portable (or mobile) electronic device such as a cell phone, a personal data assistant (PDA), a personal media player device, a wireless web-watch device, a personal headset device, an application-specific device, or a hybrid device that include any of the above functions. The computing device 1000 may also be implemented as a personal computer including both laptop computer and non-laptop computer configurations.

The present disclosure is not to be limited in terms of the particular embodiments described herein, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of this disclosure. It is also to be understood that the terminology used herein is for the purpose of describing particular embodiments only, and is not intended to be limiting.

The present disclosure is not to be limited in terms of the particular embodiments described herein, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of this disclosure. Also, the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that include A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that include A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

For any and all purposes, such as in terms of providing a written description, all ranges disclosed herein also encompass any and all possible sub ranges and combinations of sub ranges thereof. Any listed range can be easily recognized as sufficiently describing and enabling the same range being broken down into at least equal halves, thirds, quarters, fifths, tenths, and/or others. As a non-limiting example, each range discussed herein can be readily broken down into a lower third, middle third and upper third, etc. All language such as "up to," "at least," and the like include the number recited and refer to ranges which can be subsequently broken down into sub ranges as discussed above. Finally, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, various embodiments of the present disclosure have been described herein for purposes of illustration, and various modifications may be made without departing from the scope and spirit of the present disclosure. Accordingly, the various embodiments disclosed herein are not intended to be limiting.

The invention claimed is:

1. A distributed acoustic detector system, comprising:
a frame structure configured to be retained in a laser-based ophthalmological surgical system and to be aligned to an eye of a patient during therapeutic treatment of the eye of the patient with the laser-based ophthalmological surgical system;
a plurality of acoustic detectors coupled to the frame structure at a plurality of spaced apart locations from each other and each acoustic detector being electrically separated from each other acoustic detector; and
a processor communicatively coupled to the plurality of acoustic detectors and configured to analyze a plurality of detection signals generated by the plurality of acoustic detectors that are each representative of a detected acoustic wave to determine a particular location within the eye of the patient at which a microbubble formed and burst based on a time difference of arrival of the detected acoustic wave at the plurality of acoustic detectors.

2. The distributed acoustic detector system of claim 1, wherein the frame structure includes a contact lens.

3. The distributed acoustic detector system of claim 1, wherein the frame structure includes a circular perimeter and the plurality of acoustic detectors are spaced apart from each other along the circular perimeter at substantially equal intervals.

4. The distributed acoustic detector system of claim 1, wherein each of the acoustic detectors comprises a piezoelectric transducer.

5. The distributed acoustic detector system of claim 1, further comprising one or more acoustic signal generators coupled to the frame structure, wherein the one or more acoustic signal generators are configured to generate and emit interrogation acoustic waves into the eye of the patient.

6. The distributed acoustic detector system of claim 1, further comprising at least one acoustic signal generator coupled to the frame structure and configured to generate and emit interrogation acoustic waves into the eye of the patient, wherein the plurality of acoustic detectors is configured to detect echo acoustic waves of reflections of the interrogation acoustic waves from microbubbles formed on melanosomes of retinal pigment epithelial (RPE) cells of the eye of the patient in response to exposure to therapeutic radiation during the therapeutic treatment of the eye of the patient with the laser-based ophthalmological surgical system.

7. The distributed acoustic detector system of claim 1, further comprising:
   at least one acoustic signal generator coupled to the frame structure and configured to generate and emit interrogation acoustic waves into the eye of the patient; and
   the processor communicatively coupled to the plurality of acoustic detectors and configured to analyze a plurality of detection signals generated by the plurality of acoustic detectors that are each representative of a detected echo acoustic wave to determine a particular location within the eye of the patient at which a microbubble formed based on a time difference of arrival of the detected acoustic wave at the plurality of acoustic detectors.

8. The distributed acoustic detector system of claim 1, further comprising:
   at least one acoustic signal generator coupled to the frame structure and configured to generate and emit interrogation acoustic waves into the eye of the patient;
   at least one frequency detector communicatively coupled to the plurality of acoustic detectors and configured to determine frequencies of detected echo acoustic waves over time; and
   the processor communicatively coupled to the at least one frequency detector and configured to determine at least one time at which microbubbles form or burst based on frequencies of the detected echo acoustic waves as a function of time.

9. The distributed acoustic detector system of claim 1, further comprising at least one frequency detector that includes at least one of:
   a heterodyne frequency modulation (FM) receiver; or
   a digital electronic circuit that includes at least one of:
   a field programmable gate array (FPGA);
   a digital signal processor (DSP); or
   an application specific integrated circuit (ASIC).

10. The distributed acoustic detector system of claim 1, further comprising at least one frequency detector that includes a digital electronic circuit, wherein the digital electronic circuit is configured to determine the frequencies of detected echo acoustic waves over time by applying a Fourier transform to digitized detection signals generated by the plurality of acoustic detectors that are each representative of a detected echo acoustic wave.

11. The distributed acoustic detector system of claim 1, further comprising a plurality of acoustic signal generators configured to generate and emit interrogation acoustic waves into the eye of the patient, wherein the plurality of acoustic signal generators are controlled to generate and emit interrogation acoustic waves that constructively combine along a preferred direction toward a target location at which therapeutic radiation is targeted.

12. A method of therapeutic radiation dosimetry, the method comprising:
   positioning a plurality of acoustic detectors to receive acoustic wave from microbubbles formed in an eye of a patience during a therapeutic treatment of the eye of the patient with therapeutic radiation;
   illuminating the eye of the patient with the therapeutic radiation, wherein the therapeutic radiation causes the microbubbles to form on melanosomes of retinal pigment epithelial (RPE) cells of the eye of the patient during the therapeutic treatment of the eye of the patient;
   detecting, at the plurality of acoustic detectors, acoustic waves received from the microbubbles formed in the eye of the patient;
   generating detection signals by the plurality of acoustic detectors, the detection signals being indicative of an amount of therapeutic radiation exposure of the eye of the patient; and
   analyzing the detection signals generated by the plurality of acoustic detectors that are each representative of a detected acoustic wave to determine a particular location within the eye of the patient at which a microbubble formed and burst based on a time difference of arrival of the detected acoustic wave at the plurality of acoustic detectors.

13. A method of therapeutic radiation dosimetry, the method comprising:
   illuminating an eye of a patient with therapeutic radiation, wherein the therapeutic radiation causes microbubbles to form on melanosomes of retinal pigment epithelial (RPE) cells of the eye of the patient during therapeutic treatment of the eye of the patient;
   receiving, by a distributed acoustic detector system, acoustic waves from the microbubbles formed in the eye of the patient during therapeutic treatment of the eye of the patient with the therapeutic radiation, wherein the distributed acoustic detector system comprises a frame structure configured to be retained in a laser-based ophthalmological surgical system and to be aligned to the eye of the patient during therapeutic treatment of the eye of the patient with the laser-based ophthalmological surgical system and a plurality of acoustic detectors spaced apart from each other and electrically separated from each other;
   detecting at the plurality of acoustic detectors acoustic waves received from the microbubbles formed in the eye of the patient;
   generating detection signals by the plurality of acoustic detectors, the detection signals being indicative of an amount of therapeutic radiation exposure of the eye of the patient;
   analyzing, by a processor, the detection signals generated by the plurality of acoustic detectors that are each representative of a detected acoustic wave to determine a particular location within the eye of the patient at which a microbubble formed and burst based on a time difference of arrival of the detected acoustic wave at the plurality of acoustic detectors.

14. The method of claim 13, further comprising controlling the distributed acoustic detector system to emit interrogation acoustic waves from at least one acoustic signal generator into the eye of the patient, wherein detecting the acoustic waves comprises detecting echo acoustic waves of reflections of the interrogation acoustic waves from the microbubbles.

15. The method of claim 14, further comprising:
   emitting interrogation acoustic waves from at least one acoustic signal generator into the eye of the patient; and
   analyzing, by the processor, the detection signals generated by the plurality of acoustic detectors that are each representative of a detected echo acoustic wave from the interrogation acoustic waves to determine a particular location within the eye of the patient at which a microbubble formed and burst based on a time difference of arrival of the detected echo acoustic wave at the plurality of acoustic detectors.

16. The method of claim 13, further comprising:
emitting interrogation acoustic waves from at least one acoustic signal generator into the eye of the patient, wherein detecting the acoustic waves comprises detecting echo acoustic waves of reflections of the interrogation acoustic waves from the microbubbles;
determining frequencies of detected echo acoustic waves over time; and
determining at least one time at which the microbubbles form or burst based on frequencies of the detected echo acoustic waves as a function of time.

17. The method of claim 13, further comprising:
digitizing each of the detection signals; and
determining frequencies of detected echo acoustic waves by performing a Fourier transform of each of the digitized detection signals, wherein the echo acoustic wave are from reflections of interrogation acoustic waves from the microbubbles.

18. The method of claim 13, further comprising:
determining an exposure level of the eye of the patient to the therapeutic radiation based at least in part on one or more detection signals generated by one or more of the plurality of acoustic detectors; and
terminating exposure of the eye of the patient to the therapeutic radiation emitted by the therapeutic radiation source in response to the exposure level of the eye of the patient to the therapeutic radiation reaching a threshold exposure level.

* * * * *